Figure 1A:
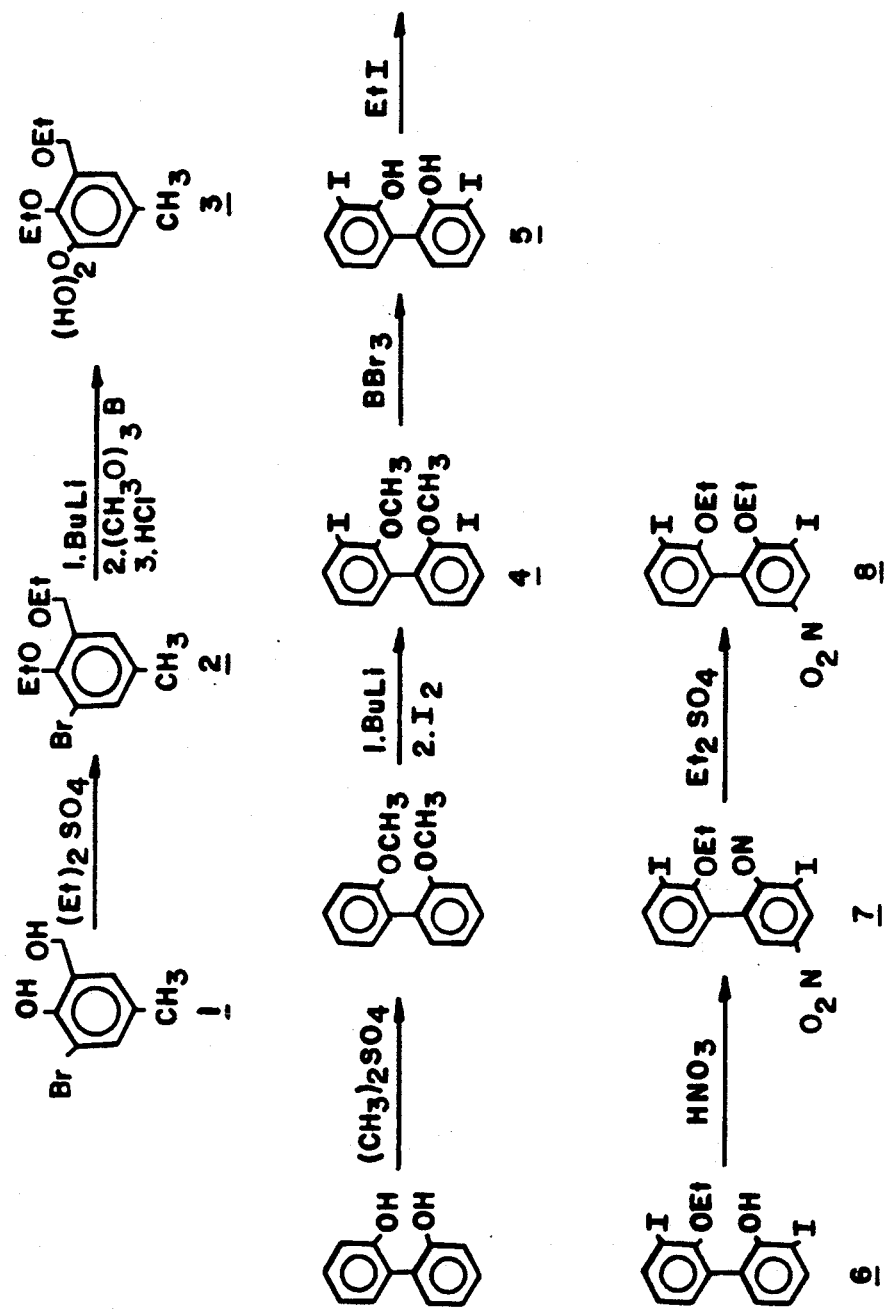

United States Patent [19]

Cram et al.

[11] Patent Number: 5,177,221

[45] Date of Patent: Jan. 5, 1993

[54] CHROMOGENIC HEMISPHERANDS AND THEIR PREPARATION

[75] Inventors: Donald J. Cram, Los Angeles, Calif.; Eddy Chapoteau, Brooklyn, N.Y.; Bronislaw P. Czech, Peekskill, N.Y.; Carl R. Gebauer, Crompond, N.Y.; Roger C. Helgeson, Canuga Park, Calif.; Anand Kumar, Southfields; Koon-Wah Leong, Ossining, both of N.Y.

[73] Assignees: Miles Inc., Tarrytown, N.Y.; The Regents of the University of California, Berkeley, Calif.

[21] Appl. No.: 564,203

[22] Filed: Aug. 8, 1990

Related U.S. Application Data

[62] Division of Ser. No. 38,679, Apr. 15, 1987, Pat. No. 4,992,381.

[51] Int. Cl.⁵ .................. C07D 323/00; C07D 215/16
[52] U.S. Cl. ..................................... 549/348; 436/79; 436/74; 549/352; 549/353; 546/160
[58] Field of Search ..................... 436/79, 74; 549/348

[56] References Cited

U.S. PATENT DOCUMENTS

| | | | |
|---|---|---|---|
| 4,367,072 | 1/1983 | Vogtle et al. | 436/501 |
| 4,421,923 | 12/1983 | Bartsch | 549/348 |
| 4,476,007 | 10/1984 | Toner et al. | 204/418 X |
| 4,505,800 | 3/1985 | Toner et al. | 204/418 |
| 4,639,424 | 1/1987 | Wong | 436/74 |
| 4,645,744 | 2/1987 | Charlton et al. | 436/74 |
| 4,649,123 | 3/1987 | Charlton et al. | 436/74 X |
| 4,659,815 | 4/1987 | Pacey et al. | 436/79 |
| 4,670,218 | 6/1987 | Gantzer et al. | 436/74 X |
| 4,708,776 | 11/1987 | Roth et al. | 204/418 X |
| 4,711,853 | 12/1987 | Pacey et al. | 436/74 |
| 4,734,375 | 3/1988 | Charlton | 436/74 |
| 4,734,376 | 3/1988 | Pacey et al. | 436/74 X |
| 4,742,010 | 5/1988 | Lin et al. | 436/74 |
| 4,762,799 | 8/1988 | Seitz et al. | 436/74 X |
| 4,859,606 | 8/1989 | Cram et al. | 436/79 |
| 4,992,381 | 2/1991 | Cram et al. | 436/79 |

FOREIGN PATENT DOCUMENTS

| | | |
|---|---|---|
| 0082518 | 6/1983 | European Pat. Off. . |
| 0141134 | 5/1985 | European Pat. Off. . |
| 3202779 | 8/1983 | Fed. Rep. of Germany . |
| 0011039 | 1/1983 | Japan . |

OTHER PUBLICATIONS

Takagi, et al., Analytical Letters, No. 10(13), pp. 1115-1122, 1977.
Takagi, et al., "Crown Compounds as Alkali and Alkaline Earth Metal Ion Selective Chromogenic Reagents", Current Chemistry, No. 121, Guest Host Complex Chemistry III, 1984, Spring-Verlag Berlin Heidelberg.
Cram, et al., J. Am. Chem. Soc., vol. 104, pp. 6827-6828, 1982.
Cram, et al., J. Am. Chem. Soc., vol. 106, pp. 3286-3292, 1984.
Artz, et al., J. Am. Chem. Soc., vol. 106, pp. 2160-2171, 1984.

Primary Examiner—C. Warren Ivy
Assistant Examiner—A. A. Owens
Attorney, Agent, or Firm—Jeffrey M. Greenman

[57] ABSTRACT

The present invention resides in the discovery of a new class of compounds defined herein as "chromogenic hemispherands" useful for the measurement of ions, in particular, ions in aqueous solution, which have the structure wherein:

(Abstract continued on next page.)

R, same or different, is hydrogen, lower alkyl, lower alkylidene, lower alkenyl, allyl or aryl;

R', same or different, is lower alkyl, lower alkylidene, lower alkenyl, allyl or aryl;

R", same or different, is hydrogen, lower alkyl, lower alkylidene, lower alkenyl, allyl or aryl;

Q is a chromogenic moiety capable of providing the appearance of or change in color, or which is otherwise capable of providing a detectable response in the presence of a particular cation;

m is 1 to about 3;

n is 0 to about 3;

A is an aliphatic or aromatic subunit, e.g.,

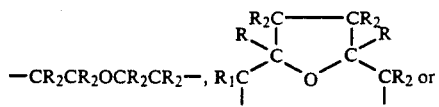, 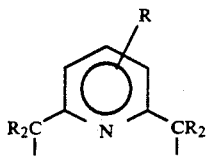

9 Claims, 6 Drawing Sheets

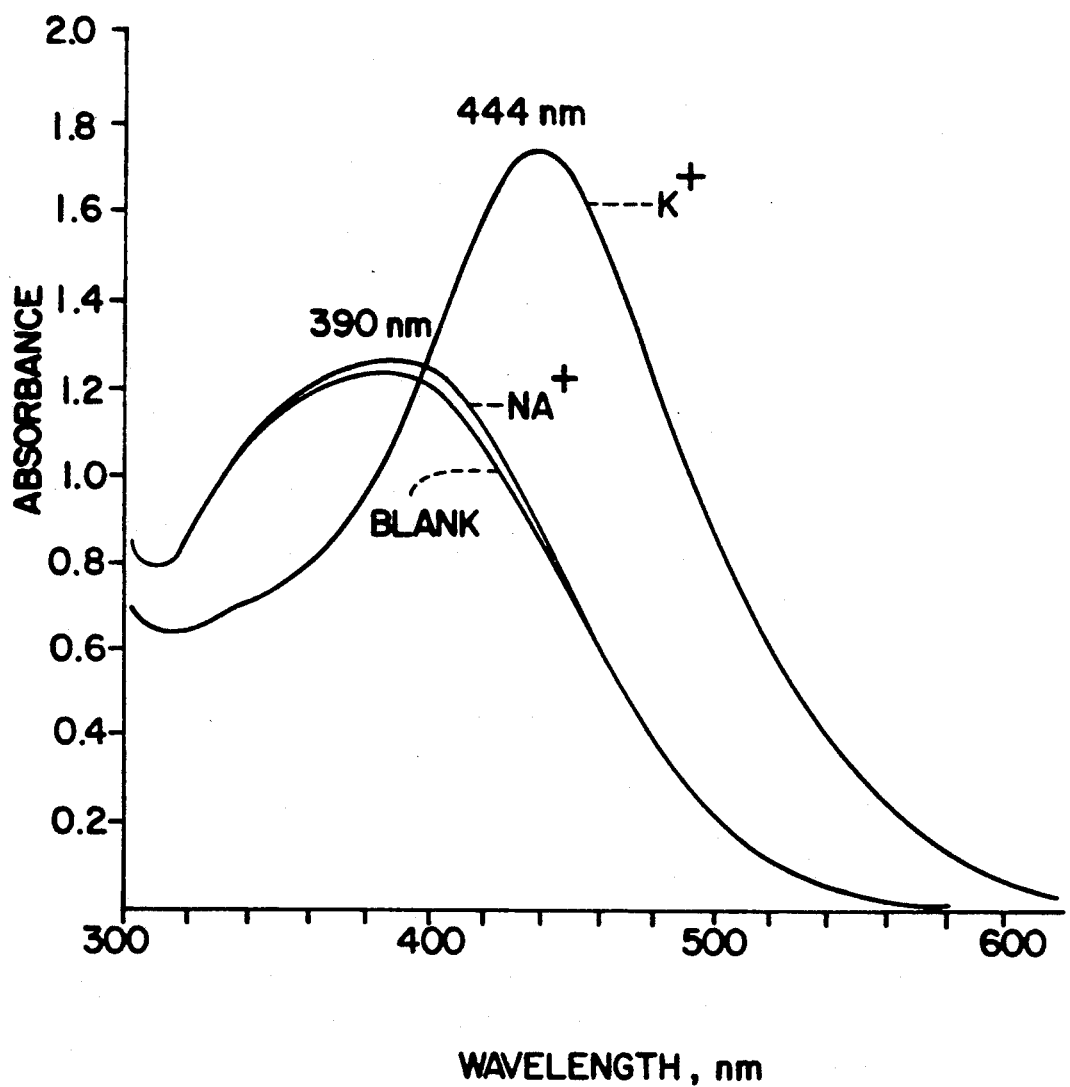

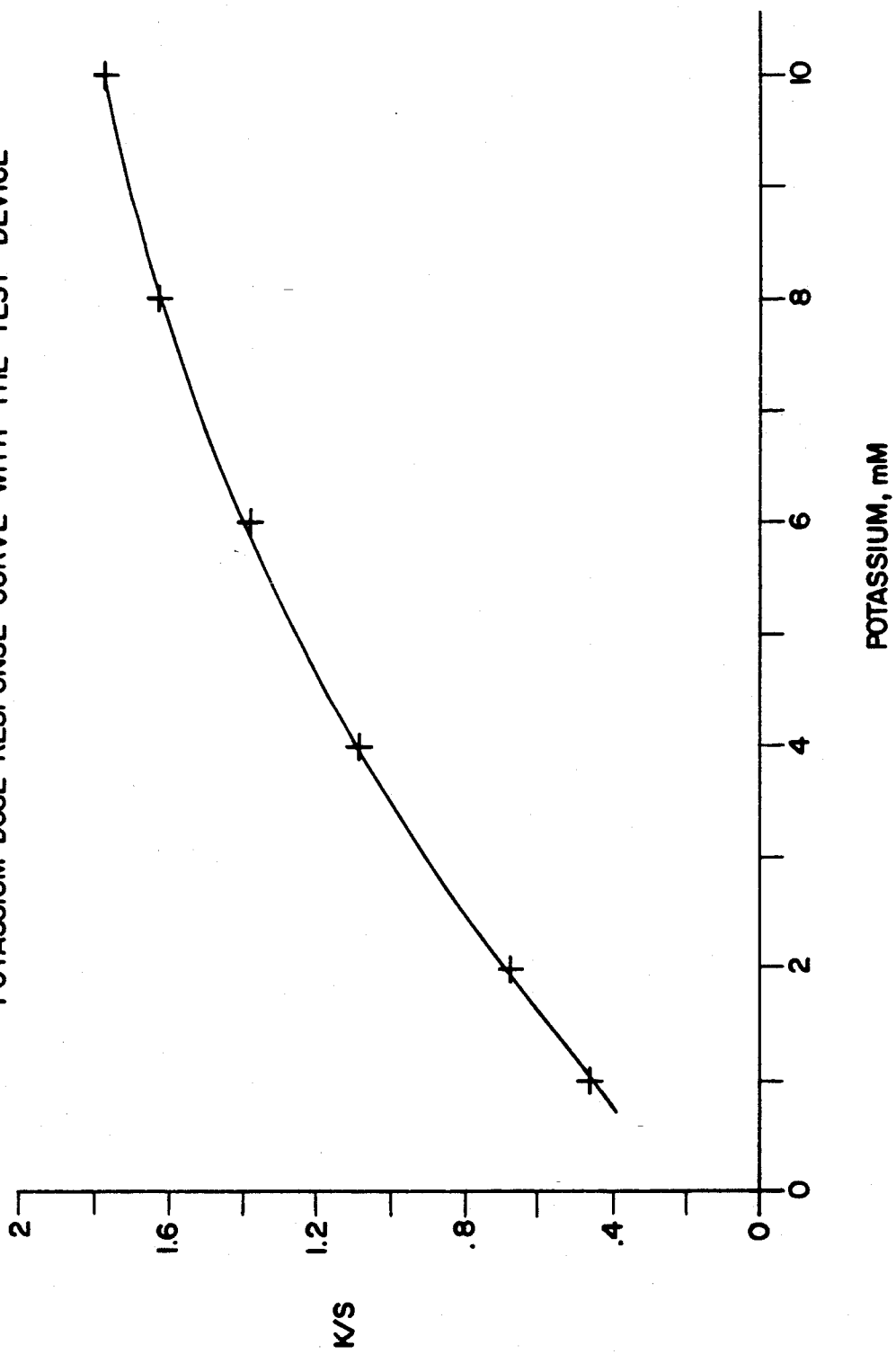

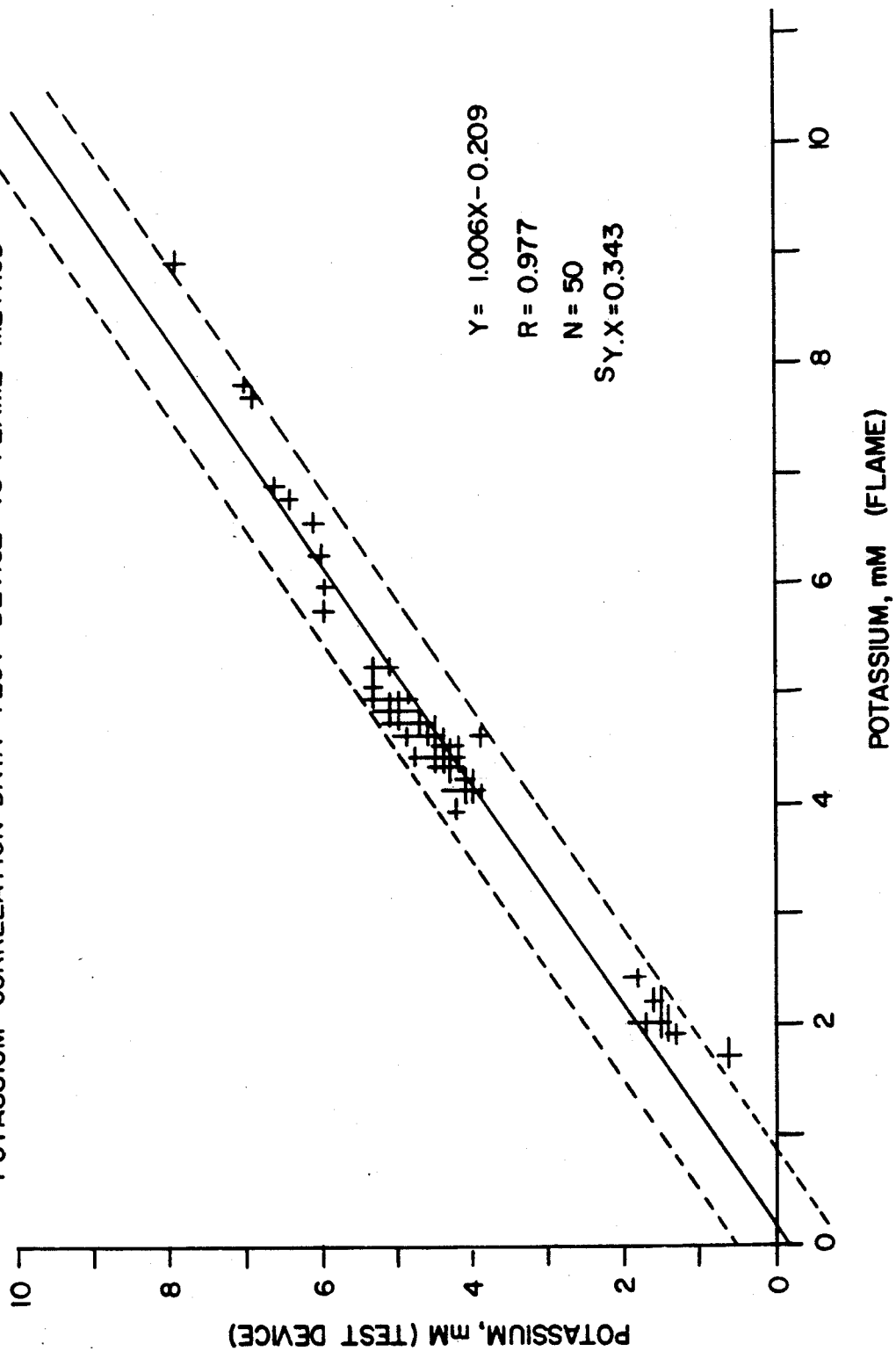

CHROMOGENIC HEMISPHERANDS AND THEIR PREPARATION

This is a divisional of co-pending application Ser. No. 07/038,679 filed Apr. 15, 1987 now U.S. Pat. No. 4,992,381.

CONTENTS

Section

1. Introduction
2. Background of the Invention
   - 2.1. Ion-selective Electrodes
   - 2.2. Liquid/Liquid Partitioning
   - 2.3. Fluorescent Anions
   - 2.4. Reporter Substances
   - 2.5. Ionophores
     - 2.5.1. Podands
     - 2.5.2. Corands
     - 2.5.3. Cryptands
     - 2.5.4. Hemispherands
     - 2.5.5. Spherands
     - 2.5.6. Cryptahemispherands
   - 2.6. Chromogenic Ionophores
   - 2.7. Synopsis
3. Brief Description of the Drawings
4. Summary of the Invention
5. Definitions
   - 5.1. "Ionophore"
   - 5.2. "Chromogenic"
   - 5.3. "Detectable Response"
   - 5.4. "Lower Alkyl, Lower Alkylidene, Lower Alkenyl"
   - 5.5. "Aryl"
   - 5.6. "Electron Withdrawing Group"
6. The Chromogenic Hemispherand
   - 6.1. Cationic Adaptability
   - 6.2. The Chromogenic Moiety
   - 6.3. Presently Preferred Embodiment
7. The Test Composition
8. The Test Device
   - 8.1. The Carrier Matrix
   - 8.2. Making the Test Device
9. Use of the Invention
10. Experimental
    - 10.1. Synthesis of a Preferred Chromogenic Hemispherand
    - 10.2. Synthesis of a Second Preferred Chromogenic Hemispherand
    - 10.3. A Preferred Aqueous System for Potassium Determination
    - 10.4. A Preferred Liquid/Liquid Partitioning System for Potassium Assay
    - 10.5. A Preferred Test Device
    - 10.6. Use of a Preferred Test Device for Potassium Determination in Serum
11. What is Claimed

1. INTRODUCTION

The present invention relates to a novel class of compounds useful for the measurement of ions, in particular ions in aqueous solution, and to a test means or device utilizing one or more of the compounds for performing such measurements. The invention provides a quick, facile way of assaying such ions whereby results are available to the assayist momentarily after merely contacting a test sample solution with the test means or device. There is no need for cumbersome, expensive electronic equipment such as ion-selective electrodes, flame photometers, atomic absorption spectrophotometers or the like. Nor is it necessary to resort to time-consuming wet chemistry techniques such as titration and other laboratory procedures. The present invention enables the analyst to merely contact the test sample with a test composition or a dry test device, test slide, or similar test means or configuration, and observe any color change or other detectable response. Finally, the present invention enables an unusually fast assay and unexpectedly high degree of selectivity, thereby permitting the detection of relatively low concentrations of an analyte ion even in solutions having relatively high concentrations of different, potentially interfering ions, while providing selectivity and accuracy to a degree heretofore unknown.

The determination of aqueous ion concentration has application in numerous technologies. In the water purification art, calcium concentration must be carefully monitored to assess the degree of saturation of an ion exchange resin deionizer. Measurement of sodium and other ions in seawater is important in the preparation of drinking water aboard a ship at sea. Measurement of the potassium level in blood aids the physician in the diagnosis of conditions leading to muscle irritability and excitatory changes in myocardial function. Such conditions include oliguria, anuria, urinary obstruction and renal failure due to shock.

Needless to say, a rapid, easy-to-perform method for determining the presence and concentration of a specific ion in aqueous samples would greatly enhance the state of these technologies, as well as any others where such quick, accurate determinations would be beneficial. Thus, for example, if a medical laboratory technician could accurately measure the potassium or sodium level of a serum, whole blood, plasma or urine sample in a matter of seconds or minutes, it would aid the physician in early diagnosis, and laboratory efficiency would increase manyfold. The present invention affords these and other unexpected advantages.

2. BACKGROUND OF THE INVENTION

Prior to the present invention, methods for determining ions in solution included flame photometry, atomic absorption photometry, ion-selective electrodes, multiple liquid phase partitioning and colorimetric slides. The use of certain compounds and compositions which selectively complex with, and therefore isolate, certain ions from the sample solution has become popular in ion-selective electrodes. These substances, known as ionophores, have the capability of selectively isolating ions from their counterions and other ions in a test sample, thereby causing a charge separation and a corresponding change in electrical conductivity in the phase containing the ionophore. Illustrative of other uses of the ion/ionophore phenomenon include ion assays utilizing membrane electrodes, liquid/liquid partitioning, fluorescence, various reporter substances, and chromogenic derivatives of certain ionophoric compounds.

2.1. Ion-Selective Electrodes (ISE)

When two solutions having different concentrations of ions are separated by an electrically conductive membrane, an electromotive force (EMF) can be generated. The EMF developed by such a system is a function of concentration or ionic activity of the solutions on either side of the membrane. This phenomenon is expressed mathematically by the well-known Nernst Equation $$E = \frac{RT}{nF} \ln \frac{\gamma 1^{\cdot}1}{\gamma 2^{\cdot}2} \qquad (1)$$

in which E is the EMF of the particular system, F is the Faraday Constant, R is the gas constant, T is the temperature in °K. and $\gamma$ and c are, respectively, the activity coefficient and molal concentrations of the ion under study. The subscript 1 designates the solution on one side of the membrane; the subscript 2 denotes the solution on the other side. The charge of the ion involved in the reaction is denoted by n.

In such membrane separation cells, the membrane can be a simple fritted glass barrier, allowing a small but measurable degree of ion diffusion from one solution to the other. Alternatively, a nonporous, electrically non-conductive film, such as polyvinyl chloride, impregnated with an ionophore can be employed. In the absence of the ionophore the film is an insulator and no EMF can be measured; when blended with an ionophore, charged ions are bound to the film and a small, measurable current can be induced to flow. Because the ionophore is selective in its affinity, and thus will bind only certain specific ions, such cells are ion selective. Any measurable EMF is due solely to the presence of those ions.

It is known that certain antibiotics, such as valinomycin, have an effect on the electrical properties of phospholipid bilayer membranes (biological membranes), such that these antibiotics effect solubilization of cations within the membrane, in the form of mobile charged complexes, thereby providing a "carrier" mechanism by which cations can cross the insulating hydrophobic or hydrocarbon interior of the membrane. Such complexes have the sole purpose of carrying the charge of the complex through the membrane. In an ISE they cause a voltage differential which can be determined between solutions on either side of the ISE membrane.

Thus, a cell for determining potassium ion can be produced through use of an ionophore specific for potassium ($K^+$), e.g. valinomycin. In the presence of $K^+$, valinomycin produces a concentration gradient across a membrane by binding and transporting the ion, thus generating a potential across the membrane. A reference concentration of $K^+$ is placed on one side of the membrane and the test sample on the other. The EMF developed is measured using external reference electrodes and used to calculate the unknown concentration from equation (1). Because only $K^+$ binds to the valinomycin in the membrane, the conductive path only appears for $K^+$. Therefore, the EMF developed is attributable solely to the $K^+$ concentration gradient across the membrane.

The current flowing across the membrane is so small that no significant quantity of $K^+$ or counterion is transported through it. Electrical neutrality of the membrane is maintained either by a reverse flow of hydrogen ions (protons), or by a parallel flow of $OH^-$.

A major difficulty in the use of such ion-selective electrodes has been the marked reduction of accuracy, selectivity and speed of response over time. Further, small changes in ion concentration produce such small changes in EMF that sophisticated voltmeter equipment is required.

Swiss Patent Application Serial No. 11428/66, filed Aug. 9, 1966, describes the use of porous membranes impregnated with macrocyclic derivatives of amino and oxy-acids in ion-sensitive electrodes. Materials used to form the membrane are glass frits and other porous membranes. Such electrodes are said to be effective in measuring ion activities.

U.S. Pat. No. 4,053,381, issued to Hamblen, et al., discloses similar technology, and utilizes an ion specific membrane having ion mobility across it.

2.2. Liquid/Liquid Partitioning

Another known application of ionophores in ion determination is through liquid/liquid partitioning. Eisenman et al., *J. Membrane Biol.*, 1, 294–345 (1969), disclose the selective extraction of cations from aqueous solutions into organic solvents via macrotetralide actin antibiotics. In this procedure, a hydrophobic ionophore is dissolved in an organic solvent immiscible with water. The technique involves shaking an organic solvent phase containing the antibiotics with aqueous solutions containing cationic salts of lipid-soluble colored anions, such as picrates and dinitrophenolates. The intensity of color of the organic phase is then measured spectrophotometrically to indicate how much salt has been extracted. Phase transfer has also been studied by Dix et al., *Angew, Chem. Int. Ed. Engl.*, 17, 857 (1978) and is reported in reviews including Burgermeister et al., *Top. Curr. Chem.*, 69, 91 (1977); Yu et al., "Membrane Active Complexones," Elsevier, Amsterdam (1974); and Duncan, "Calcium in Biological Systems," Cambridge University Press (1976).

Sumiyoshi, et al., *Talanta*, 24, 763–5 (1977) describe another method useful for determining $K^+$ in serum. In this technique serum is deproteinated by trichloroacetic acid, an indicator dye is added, and the mixture shaken with a solvent such as chloroform containing valinomycin.

Partitioning of a compound is rapid and effective between liquids, as shown by Eisenman, because of the mobility of the ionophore carrier and ions in their respective phases, which allows the transported species to diffuse rapidly away from the interface. Such a mechanism is normally impossible in the solid phase, because of the rigidity, immobility and essentially zero diffusion of materials in a solid phase.

2.3. Fluorescent Anions

Yet another approach to the measurement of ion activity in aqueous solutions utilizes fluorescent anions. Feinstein, et al., *Proc. Nat. Acad. Sci. U.S.A.*, 68, 2037–2041 (1971). It is stated that the presence of cation/ionophore complexes in organic solvents is known, but that complex formation in purely aqueous media had theretofore not been detected. Feinstein, et al., demonstrated the existence of such complexes in water through the use of the fluorescent salts 1-anilino-8-naphthalene sulfonate and 2-p-toluidinyl sulfonate.

It was found that interaction of the ionophore/cation complex with the fluorescent dyes produced enhanced fluorescence emission, increased lifetime and polarization, and significant blue-shift at the emission maxima of the fluorescence spectra. At constant concentrations of ionophore and fluorophore, the intensity of fluorescence emission was found to be a function of cation concentration.

2.4. Reporter Substances

As indicated supra, anionic dyes and fluorescers can be induced to enter the organic phase of a two-phase liquid system by the presence in that phase of a cation/ionophore complex. Thus these detectable anions can be said to "report" the presence of the cation trapped by the ionophore in the organic phase.

Other reporter substances which are not ionic in nature can be induced by the ionophore/cation complex to undergo a reaction yielding a detectable product. An example is the reaction sequence reported in U.S. Pat. No. 4,540,520 whereby a cation/ionophore complex induces a phenol to become deprotonated, thus initiating a coupling reaction to form a colored product. The so-called Gibbs Reaction is typical of such a reporter substance-producing reaction, in which 2,5-cyclohexadiene-1-one-2,6-dichloro-4-chloroimine couples with a deprotonated phenol to form a colored product and HCl.

2.5. Ionophores

The term "ionophore" embraces many diverse molecules, all of which are related by their unique capacity to bind with certain charged species to the relative exclusion of others, and which do so in a fashion which, at least to some degree, enables the ionophore molecule to electrically shield the ion from its environment. Indicative of this phenomenon is the liquid/liquid partitioning technique described above. The ionophore, because of its unique structure and its multitude of electron rich or electron deficient atoms ("donor atoms" or "receptor atoms", respectively) enables an ion such as sodium or potassium to enter a nonpolar organic phase.

Ionophores include naturally occurring compounds, such as valinomycin, as well as compounds of the structural categories of podands, corands, cryptands, hemispherands, spherands and cryptahemispherands.

2.5.1 Podands

Ions can be selectively complexed with certain acyclic compounds. For example, a linear chain which contains a regular sequence of electron rich donor atoms, such as oxygen, sulfur or nitrogen, has the capability of associating with positively charged ions to form complexes. The main structural difference between podands and other ionophores is the openness or acyclic nature of their structures. Thus, podands can be subcategorized into monopodands, dipodands, tripodands, etc. A monopodand, therefore, is a single organic chain containing donor or receptor atoms, a dipodand is two such chains connected to a central moiety capable of variable spacial orientation, and a tripodand is three chains attached to a central moiety.

2.5.2. Corands

The corands are monocyclic compounds which contain electron donor atoms or acceptor atoms, which are electron rich or deficient, and which are capable of complexing with particular cations or anions because of their unique structures. Included in this term are the crown ethers in which the monocyclic ring contains oxygen as the donor atoms. Other corands are compounds which contain an assortment of electron rich atoms such as oxygen, sulfur and nitrogen. Because of the unique sizes and geometries of particular corands, they are adaptable to complexing with various ions. In so complexing, the electron rich atoms, such as the oxygens in a crown ether, become spacially oriented towards the electron deficient cation. The carbon atom segments of the chain are simultaneously projected in a direction outwards from the ion. Thus, the resultant complex is charged in the center but is relatively hydrophobic at its perimeter.

2.5.3. Cryptands

The cryptands are the polycyclic analogs of the corands. Accordingly, they include bicyclic and tricyclic multidentate compounds. In the cryptands, the cyclic arrangement of donor atoms is three dimensional in space, as opposed to the substantially planar configuration of the corand. A cryptand is capable of virtually enveloping the ion in three dimensional fashion and, hence, is capable of strong bonds to the ion in forming the complex. As with the corands, the donor atoms can include such atoms as oxygen, nitrogen and sulfur.

2.5.4. Hemispherands

Hemispherands are macrocyclic or macropolycyclic ionophore systems, such as cryptands, whose cavities are partially preorganized for binding by the rigidity of the hydrocarbon support structure and the spatial and orientational dictates of appended groups.

2.5.5. Spherands

Spherands are macrocyclic or macropolycyclic ionophore systems whose cavities are fully preorganized by their synthesis, as opposed to becoming organized during complexing such as with an ion.

2.5.6. Cryptahemispherands

Cryptahemispherands combine the partially preorganized cavity features of the hemispherand, but contain multiple other ligand-gathering features of the cryptands.

2.6. Chromogenic Ionophores

Certain compounds have been studied which are capable not only of behaving as ionophores by forming cation complexes but which, when so complexed, exhibit a detectable formation of or change in color. Thus, experiments were published in 1977 whereby chromophoric moieties were covalently attached to ionophores to achieve a color response to potassium (Tagaki, et al., *Analytical Letters*, 10 (13), pp. 1115–1122 (1977)). There it is taught to couple covalently a chromophoric moiety such as 4-picryl-amino- to an ionophore such as benzo-15-crown-5. Moreover, U.S. Pat. No., 4,367,072 mentions many crown ethers, cryptands and podands covalently substituted with a chromophoric group, such as

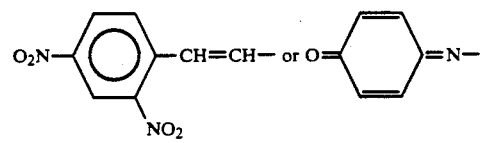

Yet another reference, German Offenlegungschrift 32 02 779, published Aug. 4, 1983 discloses a chromogenic cryptand structure.

2.7. Synopsis

Many technological developments have occurred since the early recognition that antibiotics such as valinomycin are capable of complexing certain ions and transporting them into the hydrophobic internal region of a cell membrane and, ultimately, into the cell nucleus. This basic ionophore discovery has led to the invention of a myriad of assay techniques for such ions as potassium, sodium, calcium and others; and has spawned a variety of diagnostic procedures of invaluable assistance to the chemist and physician. Moreover, countless new ionophore compounds have been discovered and invented of such chemical and structural diversity and complexity as to engender a whole new area of organic chemistry.

Certain applications of these technologies to ion determination, however, have met with problems. Although ionophores can possess high ion selectivity, the presence of high concentrations of other ions relative to the ion of interest can lead to interference in the desired result. Thus, if an ionophore were to have a specificity ratio of 50:1 for complexing with ion $X^+$ over ion $Y^+$, nevertheless if $Y^+$ were present in solution at a concentration 50 times that of $X^+$, the resultant selectivity of the system for $X^+$ would be diminished to such a great extent as to render the ionophore practically useless as an assay reagent for $X^+$. Such disparity of concentrations occurs, for example, in blood where normal sodium/potassium concentration ratios are in the neighborhood of 35:1.

Moreover, some prior art assays utilizing prior art ionophores have heretofore required a highly alkaline medium in order to function usefully, and aspects which contribute to poor shelf life as well as corrosiveness. Such systems also require a hydrophobic phase to contain or segregate the ionophore from the aqueous test sample, thus leading to organic/aqueous systems which respond relatively slowly.

Thus, it would be desirable to greatly increase selectivity in a chromogenic ionophore, thereby overcoming interference from competing ions present at much higher concentrations. Likewise, it would be desirable to obviate the need for harshly alkaline conditions and a multiphasic system. These and other unexpected advantages have been realized through utilizing the unique compounds described herein.

3. BRIEF DESCRIPTION OF THE DRAWINGS

The appended drawings are presented to further describe the invention, and to assist in its understanding through clarification of its various aspects.

Figure 1B:
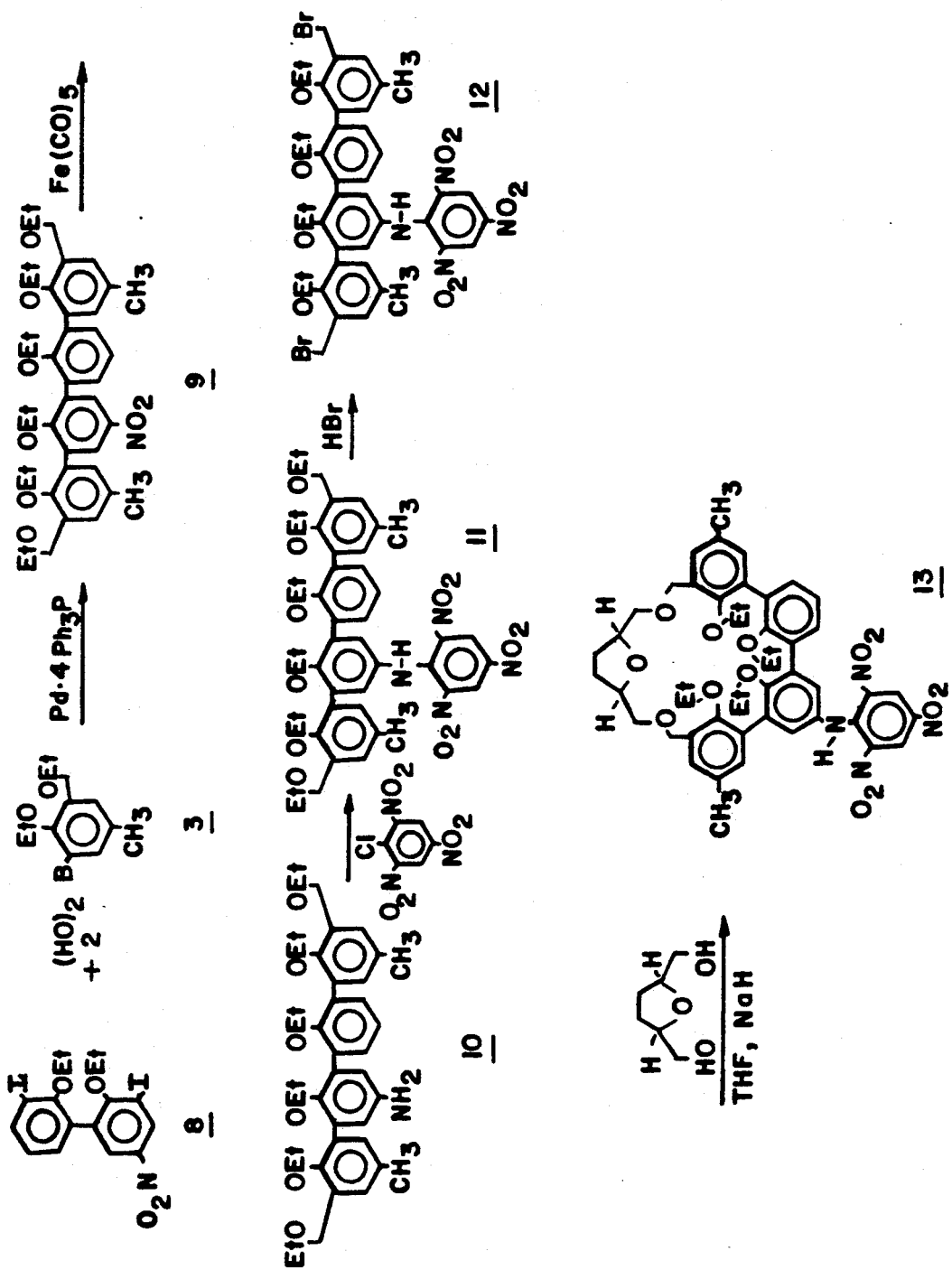

FIG. 1 describes a reaction pathway for synthesizing a preferred chromogenic hemispherand discussed in Section 6.3 herein as compound (IV) and designated in the reaction pathway as compound 13.

Figure 2:
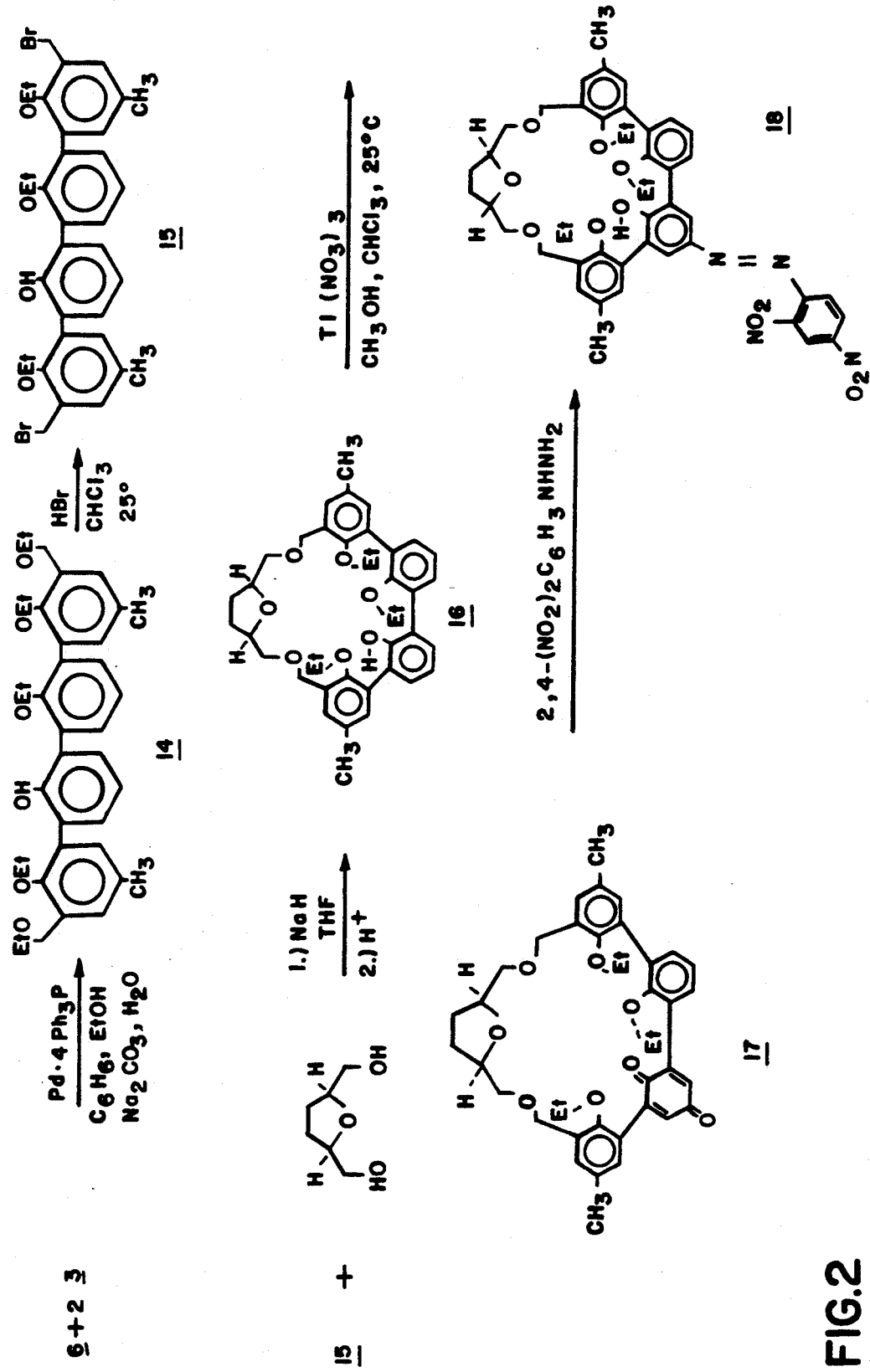

FIG. 2 describes the reaction pathway for synthesizing a second preferred chromogenic hemispherand designated as compound 18.

FIG. 3 shows the effect on light absorbance at various wavelengths for an embodiment of the invention described in Section 10.4 herein.

FIG. 4 provides a dose/response curve for various potassium levels utilizing the test device of the present invention described in Section 10.5 herein.

FIG. 5 shows the comparison between the results obtained by the test device of the present invention and a reference flame method.

4. SUMMARY OF THE INVENTION

Briefly stated, the present invention resides in the discovery of a new class of compounds defined herein as "chromogenic hemispherands", which have the structure (I):

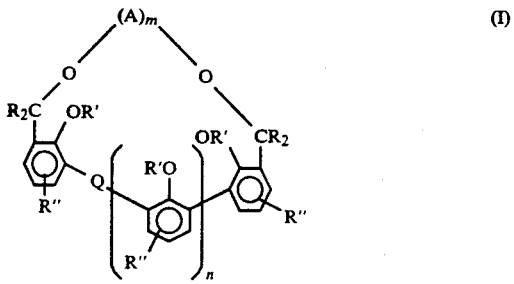

(I)

wherein:
R, same or different, is hydrogen, lower alkyl, lower alkylidene, lower alkenyl, allyl or aryl;
R', same or different, is lower alkyl, lower alkylidene, lower alkenyl, allyl or aryl;
R", same or different, is hydrogen, lower alkyl, lower alkylidene, lower alkenyl, allyl or aryl;
Q is a chromogenic moiety capable of providing the appearance of or change in color, or which is otherwise capable of providing a detectable response in the presence of a particular cation;
m is 1 to about 3;
n is 0 to about 3;
A is an aliphatic or aromatic subunit, e.g., $-CR_2CR_2OCR_2CR_2-$,

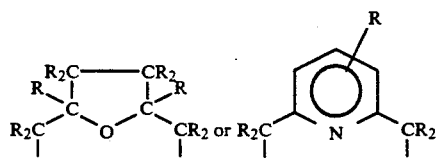

This discovery led to further discoveries, including a composition for detecting the presence of an ion in solution, such as potassium and sodium, and a method for its use. The composition comprises the compound and a buffer capable of providing a pH in the range of about 7-11. Incorporation of the composition into a carrier matrix provides a dry test device for use in determining specific ions in solution. Both the composition and the device are utilized by contacting either with a test sample suspected of containing the ion of interest, and observing a detectable response.

Finally, the process for making the compounds of the present invention is a further part of the present invention, entailing truly innovative organic synthesis, and which enabled the synthesis of a preferred embodiment of the unique compounds of the present invention. The preferred processes comprise a synthesis sequence such as are described in FIGS. 1 and 2.

The scope of the invention, including the compound, composition and test device; and their use, synthesis and preparation, and experimental results are set forth in Sections 4-10 herein, and in the appended claims.

5. DEFINITIONS

Certain terms used in the present discussion should at this point be mentioned to assure that the reader is of the same mind as the authors as to their respective meanings. Thus the following definitions are provided to clarify the scope of the present invention, and to enable its formulation and use.

5.1. Ionophore

The term "ionophore" includes, broadly, molecules capable of forming a complex with an ion in solution. For example the cyclic polypeptide, valinomycin, binds selectively to potassium ions in solution to form a cationic complex. Also included in the term are podands, corands, cryptands, hemispherands, cryptahemispherands and spherands.

5.2. Chromogenic

As used herein, "chromogenic" is intended as meaning that characteristic of a chemical system whereby a detectable response is generated in response to an external stimulus. Thus, for example, a hemispherand is chromogenic where it is capable of exhibiting a detectable response upon complexing with an ion, which detectable response is not limited solely to change in color as defined below.

5.3. Detectable Response

By the term "detectable response" is meant a change in or appearance of a property in a system which is capable of being perceived, either by direct observation or instrumentally, and which is a function of the presence of a specific ion in an aqueous test sample. Some examples of detectable responses are the change in or appearance of color, fluorescence, phosphorescence, reflectance, chemiluminescence, or infrared spectrum which are referred to generally as chromogenic responses. Other examples of detectable responses may be the change in electrochemical properties, pH and nuclear magnetic resonance.

5.4. Lower Alkyl, Lower Alkylidene, Lower Alkenyl

The term "lower alkyl", as used in the present disclosure includes an alkyl moiety, substituted or unsubstituted, containing about 1–4 carbon atoms. Included in the meaning of lower alkyl are methyl, ethyl, n-propyl, isopropyl, n-butyl, sec-butyl and tert-butyl. These may be unsubstituted, or they may be substituted provided any such substituents do not interfere with the operation or functioning of the presently claimed test means or device in its capability to detect ions. "Lower alkylidene" is used in the same context as "lower alkyl", but designates an alkylene or alkylidine group (i.e., a divalent alkyl) having 1–4 carbon atoms. Thus, lower alkylidene includes methylene, ethylidene, n-propylidene, isopropylidene, n-butylidene, sec-butylidene and tert-butylidene. "Lower alkenyl" means vinyl or lower alkyl substituted vinyl.

Substituent groups can be selected with a wide degree of latitude, although in general they are chosen to accommodate the intended use of the ionophore of the present invention in complexing with a particular cation. Thus in the case where the hemispherand is designed to complex with a cation such as potassium, the substituent is usually electrically neutral, such as hydrogen, methyl or ethyl.

5.5. Aryl

By the term "aryl" is meant groups having one or more six-membered aromatic ring systems. Such ring systems can be heterocyclic, such as pyridinyl ($NC_5H_4$—), or can be monocyclic, such as phenyl ($C_6H_5$—), benzyl ($C_6H_5CH_2$—) and naphthyl. Aryl groups can be substituted or unsubstituted, provided that in the former case the substituent does not interfere with the intended utility of the invention, i.e., the detection of ions in solution.

As in the case of substituent groups for lower alkyl and alkylidene, a wide latitude of substitution obtains for aryl groups, depending on the use of the ultimate chromogenic hemispherand.

5.6. Electron Withdrawing Group

By the term "electron withdrawing group" is meant substituent groups such as $NO_2$, $CF_3$, $CN$, $COOR$.

6. THE CHROMOGENIC HEMISPHERAND

The chromogenic hemispherand of the present invention, generically depicted as compound (I) in Section 4, supra, allows a significant degree of latitude as to its geometry and chemical nature, dependent upon selection of the variable parameters such as R, R', R", A, Q, m and n. It is careful selection of these parameters that permits tailoring of the molecule to alter ion selectivity.

Thus by following the teachings herein, molecules can be custom synthesized such that the internal cavity of the cyclic structure can vary greatly as to its physical dimensions, and can be rendered more or less electron-rich.

As a result, very high selectivity for one ionic species in the presence of one or more other ions can be achieved. For example, the Experimental section, Section 10, infra, illustrates the measurement of potassium concentration in solutions which contain relatively high concentrations of sodium. Thus, it is not only the structure and chromogenicity of the present compound which render it unique, but also, and perhaps more importantly, its adaptability to being fashioned to suit the intended ion of interest, thereby achieving heretofore unattainable selectivity for one type of ion in solution in the presence of another, even when the concentration of the latter far outstrips the former.

6.1. Cationic Adaptability

The chromogenic hemispherands of the present invention can be made adaptable to the detection of cations. The electron-rich oxygen atoms in the molecule render it an electron-rich environment conductive to receiving and complexing with a cation. Moreover, because of the unique steric configurational aspects of the cavity of the molecule, contributed in part by the aromatic chain of the cyclic structure, the molecule can virtually "lock in" the entrapped ion, thereby dramatically increasing the association constant, $K_a$, of the complex. Other ions in the test sample which might be attracted by the electron-rich cavity are either too large to penetrate it or too small to be held by the cavity geometry and structure, thus leading in both cases to a very low $K_a$ for competing ions in comparison to that of the ion for which the ionophore has been tailored.

6.2. The Chromogenic Moiety

Compound I includes as part of its structure a particular kind of chemically configured moiety, Q, which is capable of changing its physico-chemical characteristics when a complex is formed by an ion and compound (I). That is to say, if the target ion, i.e., the ion for which the structure of (I) has been tailored to selectively accept to form an ionophore/ion complex, is present in a test sample, whether or not other ions are present, a detectable change in those physico-chemical properties takes place. This capability of Q to exhibit such a response to complexation contributes greatly to the usefulness of compound (I) in assaying the analyte, or target, ion.

Whereas the concept of the chromogenic moiety Q is very broad, including within its scope a plethora of known and yet-to-be-discovered chemical and physical configurations, nevertheless several common threads exist among them, and are possessed by each. As the structure (I) indicates, Q must be divalent. Thus it is capable of bonding within the aromatic chain of the cyclic structure through at least two covalent bonds. Secondly, as mentioned above, it must be capable of taking on different attributes when compound (I) is complexed with an ion than when compound (I) is in its uncomplexed state.

As presently contemplated, it is preferred that Q have the generic structure II:

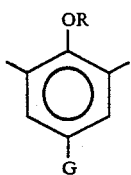

(II)

in which R is as defined supra and G is a chemical moiety which, when attached as depicted, acts by itself or in concert with the rest of the depicted structure (II) to form a detectable response to a complexed ion. Thus the concept of G is broad, and includes, but is not limited to, such chemical moieties as

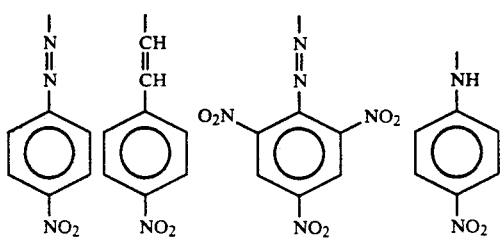

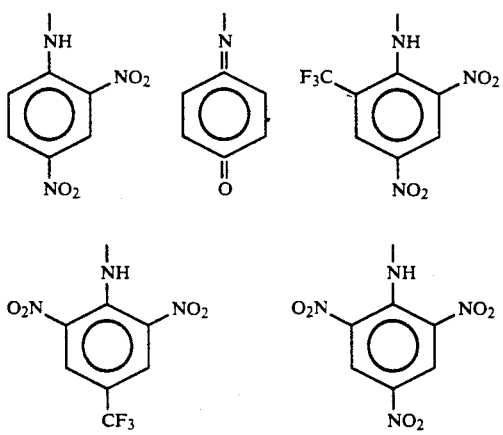

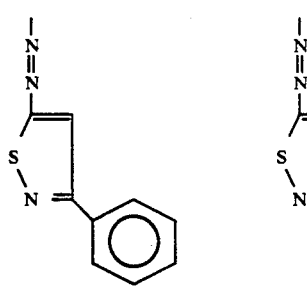

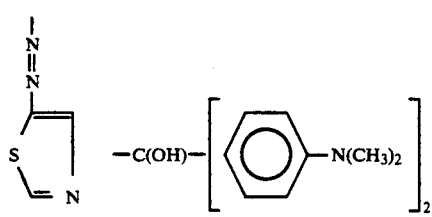

as well as any other moiety, known or to be discovered, which imparts to Q the desired detectability. Especially preferred for use as group G are 2,4,6-trinitroanilino; 2,6-dinitro-4-trifluoromethylanilino; 2,4-dinitro-6-trifluoromethylanilino; 4-nitroanilino; 4-nitrophenylazo; 4-nitrostyryl; and 4-benzoquinonmonoimino. It has been found that compound (I) is especially useful when Q has the structure

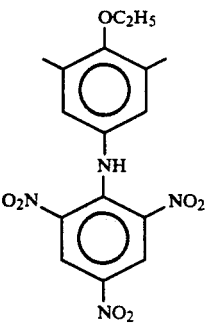

(III)

6.3. Presently Preferred Embodiment

Of the myriad compounds embodied by the present disclosure, one which has been found especially selective in the determination of K+, such as in blood, serum, and urine, is the variation of compound (I) having the structure

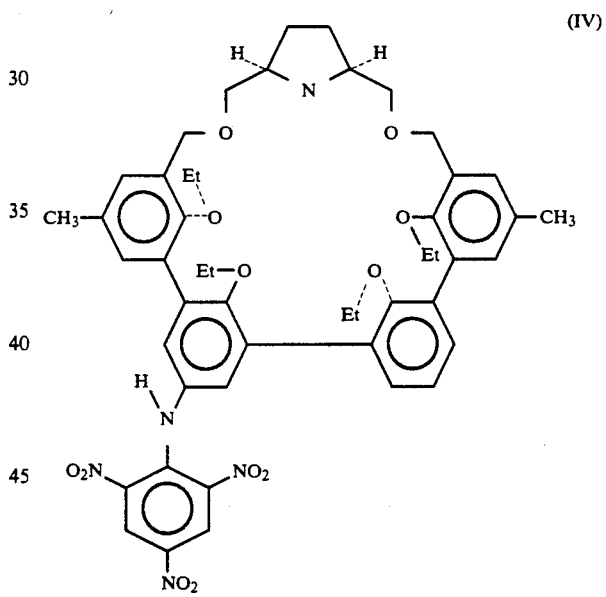

(IV)

The compound (IV) is derived from compound (I) wherein:
Q is compound (III);
R is hydrogen;
R' is ethyl (designated as Et in structure (IV);
R" is methyl;
A is

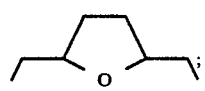

and
m, n are 1.

The chromogenic hemispherand (IV) has been found to exhibit unusually high selectivity for potassium ion, even in solutions having many times higher concentrations of other monovalent cations such as sodium. Moreover, compositions useful in such analyses can be formulated and used at a relatively mild pH, such as in the range of about 7-11, preferably between 8 and 10.

7. THE TEST COMPOSITION

The discovery of the compounds previously described prompted further research which led to the formulation of a test composition or reagent mixture, which could be useful for detecting the presence of certain ions, such as potassium, sodium, lithium, and others. Such test composition includes, in addition to compound (I), a solvent system described below, and a buffer to provide a pH environment of about 7 to about 11. Preferably the buffer provides a pH of about 8 to 10. In addition, the test composition may contain manufacturing excipients, stabilizers, surfactants and other inert ingredients, all of which are easily within the understanding of one skilled in the art, or which could be routinely determined at the bench without the need for undue experimentation.

The solvent system noted above may include water and water miscible organic solvents in proportions to obtain maximum sensitivity.

Cyclic ethers, glycol ethers, amides, aliphatic alcohols with, for example, three to eight carbon atoms and/or sulfoxides possess excellent photometric and visually evaluable color gradations with these compounds and are suitable water-miscible organic solvents useful in the present invention.

Dioxane and tetrahydrofuran are particularly suitable as cyclic ether solvents, while ethylene glycol monoalkyl ethers, particularly methyl, ethyl, propyl and butyl cellosolve, are suitable as glycol ether solvents, and formamide, dimethylformamide (DMF), pyrrolidone and N-alkylpyrrolidones, e.g., N-methylpyrrolidone (NMP), are suitable as amide solvents.

Aliphatic alcohols such as methanol and ethanol are also suitable, but better results are obtained in alcohols with three to eight carbon atoms such as isopropanol, n-propanol, butanols, amyl alcohols, hexanols, heptanols and octanols.

Dimethyl sulfoxide is also a suitable solvent.

It has been found that a large number of water-miscible organic solvents, such as, for example, acetone, methyl ethyl ketone and glacial acetic acid are unsuitable as reaction media.

Because of the importance of maintaining pH at a specific level in making accurate cation determinations, buffer may be included in compositions of this invention for the purpose of controlling the pH. Suitable buffers for maintaining the pH include cyclohexylaminopropanesulfonic acid (CAPS), cyclohexylaminoethanesulfonic acid (CHES), triethanolamine, diethanolamine, ethanolamine, 2-naphthalene sulfonic acid, and salicyclic acid. Preferably, in making a cation determination, the pH of the composition is maintained at about 7-11.

In use the test sample is merely contacted with the composition and the detectable response is observed. In the case of the compound (IV), it has been found convenient to assess the response as light absorbed such as at 440 nanometers (nm). To a small amount of an aqueous test sample is added a relatively large volume of a solution of the compound (IV) at a pH of about 8-10. The mixture is put into a cuvette and observed spectrophotometrically at about 440 nm. Experiments using varied known potassium concentrations yield a dose/response curve enabling clear correlation between change in absorbance corresponding to various potassium concentrations in the millimolar (mM) range.

8. THE TEST DEVICE

As the discovery of chromogenic compound (I) led to a test composition useful for detecting certain ions, so the composition led to a test device, thereby still further extending the utility of the basic discovery comprising the overall invention. Thus, by incorporating a suitable carrier matrix with the test composition, a test device is obtained which facilitates ion assay yet further.

Such a device lends itself to dry storage when not in use, thus enabling long shelf-life, and can be pressed into service immediately simply by contacting it with a small portion of the test sample, be it blood, serum, urine or other aqueous solution to be assayed. It can take on such formats as a dip-and-read strip for urine or a test slide for use with an automatic blood analyzer, or can from a multilayer structure such as is described in U.S. Pat. Nos. 3,992,158 and 4,292,272.

8.1. The Carrier Matrix

It is desirable that the carrier matrix comprise a porous or wettable material. Thus, in a single layer format the carrier matrix can be formed from materials such as paper, cardboard, porous polymers, polymer fiber and natural felts, and other suitable materials. Especially preferred as carrier matrix materials are filter paper, and porous high density polyethylene. In a multilayer analytical element format, the buffer can be stored in an upper layer and the chromogenic hemispherand in a lower layer in a superposed laminar fashion. The matrices for these layers can be formed from materials such as gelatin, water soluble or water swellable polymers, and other suitable materials. In addition to these two layers, a spreading layer, a reflecting layer and a support material can be incorporated to form an integral analytical element.

8.2. Making the Test Device

The device is prepared by incorporating the carrier matrix with the test composition or reagent mixture, and, if desired, providing the dried matrix with a support.

Thus the test composition is applied to the matrix by innoculating the surface of the matrix or by dipping it into a solution of the composition. The thus-impregnated matrix can then be dried at room temperature or at elevated temperatures, provided the temperature is not so high as to deleteriously affect the composition.

The dried, impregnated carrier matrix can then be mounted, if desired, on a suitable support such as a circumferential frame which leaves the matrix exposed in the middle; or the matrix can be mounted at one end of a plastic strip, the other end serving as a convenient handle.

Another way of making the test device, for the analysis of potassium for instance, can comprise the treatment of a porous high density polyethylene matrix with a surfactant to render it wettable, the impregnation of a reagent mixture containing compound (IV), a binder and a buffer, and the drying of the reagent mixture on the porous matrix.

In use the test sample is contacted with the surface of the test device and the detectable response is measured at 580 nm or other wavelength on a reflectometer. Experiments using varied known potassium concentrations yield a dose/response curve enabling clear correlation between changes in percent reflectance and potassium concentration in the millimolar range.

9. USE OF THE INVENTION

The present invention can be adapted for use in carrying out a myriad of ion assays, both manually and on automated systems, which assays are applicable to a broad field. Not only is clinical chemistry part of that field, but also chemical research, chemical process control, and quality assurance are a few of the many possible applications of this technology. The composition and test device are well suited for use in clinical testing of body fluids such as blood, blood serum and urine, since in this work a large number of repetitive tests are frequently conducted, and test results are often needed soon after the test sample is taken from the patient.

The test composition and device are used by contacting with the test sample, and observing a detectable response. In a typical analytical procedure, a portion of test sample is placed on the test device for a sufficient period of time (such as several minutes). If desired, excess sample may be removed, such as by washing in a gentle stream of water with subsequent blotting with tissue paper, or washing in a gentle stream of water.

If the ion under analysis is present in the test sample, the complex of ionophore and ion will form, and a detectable response will appear. Where the moiety Q on compound (I) forms or changes color in response to the complex, such response is observed, either with the naked eye or instrumentally. Where Q is a fluorophore such as fluoroscein, a fluorescence spectrophotometer can be utilized to measure the detectable response formed in the test device (here, the appearance of or change in fluorescence). Other techniques useful in observing a detectable response include reflectance spectrophotometry, absorption spectrophotometry and light transmission measurements.

When the test sample is blood serum, transmission or reflectance techniques can be used to detect and quantify the presence of any reaction products, the formation of which serves as the detectable response. In this case radiant energy such as ultraviolet, visible or infrared radiation, is directed onto the surface of the test device and the output of that energy from the surface is measured. Generally, electromagnetic radiation in the range of from about 200 to about 900 nm has been found useful for such measurements, although any radiation permeating the test means and which is capable of signifying the occurrence or extent of the response can be used.

Various calibration techniques are applicable as a control for the analysis. For example, a sample of analyte standard solution can be applied to a separate test means as a comparison or to permit the use of differential measurements in the analysis.

In accordance with one preferred embodiment the method of analysis comprises:
(a) preparing a reagent mixture consisting essentially of a first organic solvent having low vapor pressure and high boiling point, a second organic solvent that is more volatile than first solvent, a compound of structure (I) of the invention, and a buffer;
(b) adding the reagent mixture to the test device;
(c) evaporating the second solvent of the reagent mixture;
(d) adding the sample to the test device; and
(e) measuring reflectance of the surface of the device.

Step (a) advantageously incorporates both solvents and the organic buffer in one step, and eliminates the need for a drying step between solvent addition and buffer addition.

Preferred reagents comprise a first solvent selected from the group consisting of trialkylphospate, tryarylphosphate, dialkyladipate, dialkylsebacate, dialkyphthalates and a second solvent selected from the group consisting of cyclohexanone, dioxane and tetrahydrofuran.

Preferred reagents further comprise one or more organic buffers. Examples of suitable organic buffers include triethanolamine, diethanolamine, ethanolamine, imidazole, 2-naphthalene sulfonic, salicylic acid and p-toluene sulfonic acid. Suitable buffers maintain a pH in the range of about 7 to about 11, preferably at about 8 to 10.

10. EXPERIMENTAL

A series of experiments was performed to investigate various aspects of the present invention. A description of experimental procedures and results is provided here to assist in the understanding of the basic concepts as well as to fully and clearly described preferred embodiments.

10.1. Synthesis of a Preferred Chromogenic Hemispherand

An experiment was performed to synthesize a preferred embodiment of compound (I), supra. The chromogenic hemispherand prepared in this experiment is referred to in Section 6.3 as the compound (IV). The reaction pathway is depicted in FIG. 1, the chromogenic hemispherand designated compound 13.

Preparation of Compound 2

To a solution of 40 g (0.18 mol) of 1[1] in 1 L of THF under Ar at 0° C. was added 30 g (0.63 mol) of NaH (50% in mineral oil). After warming to 25° C., 94 g (0.61 mol) of diethyl sulfate was added and the mixture was refluxed 18 h, cooled to 0° C. and $CH_3OH$ added to decompose the excess NaH. Concentration of the mixture of 200 mL and dilution with $CHCl_3$ (0.5 L) and saturated aqueous NaCl (0.6 L) gave an organic layer which was dried, evaporated and the residue was dissolved in 100 mL of cyclohexane and chromatographed on silica gel (500 g). Elution of the column with benzene-cyclohexane (1:4) gave 33 g (66%) of 2 as a colorless oil. The mass spectrum (70 eV) gave molecular ion at m/e 272 -$Br^{79}$. The $^1H$ NMR spectrum (200 MHz, $CDCl_3$) gave absorptions at δ 1.25 (t, $CH_2CH_3$, 3H), 1.43 (t, $CH_2CH_3$, 3H), 2.29 (s, $ArCH_3$, 3H), 3.98 (q, $OCH_2$, 2H), 4.5 (q, $OCH_2$, 2H), 7.16 (d, Ar$\underline{H}$, 1H) and 7.29 (d, Ar$\underline{H}$, 1H).

[1] 2-Bromo-4-methylphenol (Aldrich Chemical Co.) was convereted to 1 by the published procedure: See Katz, H. E.; Cram, D. J. *J. Am. Chem. Soc.* 1984, 106, 4977–4987.

Preparation of Compound 3

To a solution of 29 g (106 mmol) of 2 in 400 mL of THF under Ar at −78° C. was added 45 mL of 2.4M butyllithium (hexane). After stirring 8 min, the lithiation solution was cannulated over 8 min into 96 g (0.92 mol) of trimethyl borate in 250 mL of THF at −78° C. The mixture was stirred 30 min at −78° C., warmed to 0° C. over 45 min, diluted with 400 mL of 2N hydrochloric acid, and stirred 1 h at 25° C. Ether (0.5 L) was added, the mixture was stirred 6 h at 25° C., and the layers were separated. The aqueous layer was extracted with fresh ether (2×200 mL). The combined ether extracts were extracted with 3N aqueous NaOH (4×200 mL). The base extracts were cooled to 5° C. and acidified to pH 1 with concentrated hydrochloric acid. Extraction of the aqueous solution with ether (3×200 mL) and evaporation of the ether extracts (no drying) at 25°/30 mm gave ~20 g (80%) of a moist oil which was stored at 5° C. and used without further purification.

Preparation of Compound 5

To a solution of 20 g (43 mol) of 3,3'-diiodo-2,2'-dimethoxy-1,1'-biphenyl[2] 4 in 1 L $CH_2Cl_2$ at −10° C. was added 37 g (0.15 mol) of $BBr_3$. The mixture was warmed to 25° C., stirred 6 h, cooled at 0° C., and the excess $BBr_3$ was decomposed by dropwise addition of $H_2O$. Addition of 400 mL of $H_2O$ and extractive workup gave the crude product which was recrystallized from $CH_2Cl_2$-cyclohexane (300 mL of 1:2) to give 17.5 g (93%) of a white solid, mp 157°-158° C. The mass spectrum (70 eV) showed a molecular ion at m/e 438.
[2]Cram, D. J.; deGrandpre, M.; Knobler, C. B.; Trueblood, K. N. *J. Am. Chem. Soc.* 1984, 106, 3286-3292.

The $^1H$ NMR spectrum (200 MHz, $CDCl_3$) showed absorptions at δ 5.87 (s, O$\underline{H}$, 2H), 6.80 (t, Ar$\underline{H}$, 2H), 7.22 (m, Ar$\underline{H}$, 2H) and 7.75 (m, Ar$\underline{H}$, 2H).

Preparation of Compound 6

To a mixture of 16.5 g (37.7 mmol) of 5 and 21.5 g (0.14 mol) of ethyl iodide in 110 mL acetone under Ar at 25° C. was added 5.5 g (39.8 mmol) of $K_2CO_3$, and the suspension was stirred for 72 h. The acetone and excess ethyl iodide were evaporated and the residue was partitioned between $CH_2Cl_2$ (400 mL) and 10% aqueous NaCl (500 mL). Extractive workup and concentration of the organic solution to 50 mL was followed by chromatography on 300 g alumina (MCB, activated) made up in benzene. Elution of the column with benzene gave 48 g (26%) of 3,3'-diiodo-2,2'-diethoxy-1,1'-biphenyl as a white foam. Further elution of the column with ethyl ether gave 12.3 g (70%) of 6 as a white foam. The mass spectrum gave a molecular ion (70 eV) at m/e 466. The $^1H$ NMR spectrum (200 MHz, $CDCl_3$) showed absorptions at δ 1.23 (t, $CH_2C\underline{H}_3$ 3H), 3.73 (q, $OC\underline{H}_2$, 2H), 6.77 (t, Ar$\underline{H}$, 1H), 6.97 (t, Ar$\underline{H}$, 1H), 7.30 (m, Ar$\underline{H}$, 2H) and 7.82 (m, Ar$\underline{H}$, 2H).

Preparation of Compound 7

To a solution of 1.05 g of 6 in 40 mL of $CH_3CO_2H$ was added 0.5 mL of 70% $HNO_3$. The mixture was stirred 30 min, diluted with 20 mL of $H_2O$ and the resulting suspension stirred 2 h at 25° C., filtered, and dried at 25° C. under vacuum. This material was recrystallized from $CH_2Cl_2$—$C_2H_5OH$ to give 640 mg (56%) of pale yellow crystals, mp 132°-134°. The mass spectrum (70 eV) gave the expected molecular ion at m/e 511. The $^1H$ NMR spectrum (200 MHz, $CDCl_3$) gave absorptions at δ1.27 (t, $C\underline{H}_3$ 3H), 3.82 (q, $C\underline{H}_2$, 2H), 7.05 (t, Ar$\underline{H}$, 1H), 7.93 (m, Ar$\underline{H}$, 1H), 8.26 (d, Ar$\underline{H}$, 1H) and 8.71 (d, Ar$\underline{H}$, 1H).

Preparation of Compound 8

A suspension of 0.61 g (1.2 mmol) of 7, 2.0 g (13 mmol) of diethyl sulfate and 2.5 g of potassium carbonate in 75 mL or acetone under $N_2$ was refluxed 8 h, evaporated under reduced pressure, and the residue was dissolved in 10% $NH_4OH$ and $CHCl_3$ (300 mL of each), stirred 1 h, and the layers were separated. The organic extract was dried, concentrated to 10 mL, and added to an $Al_2O_3$ column (50 g) made up in benzene. Elution of the column with benzene (1 L) gave 594 mg (92%) of 8 as a colorless glass. The mass spectrum (70 eV) gave the expected molecular ion at m/e 539. The $^1H$ NMR spectrum (200 MHz, $CDCl_3$) gave absorptions at δ 1.13-1.20 (m, $C\underline{H}_3$, 6H), 3.61-3.47 (m, $C\underline{H}_2$, 4H), 6.93 (t, Ar$\underline{H}$, 1H), 7.37 (m, Ar$\underline{H}$, 1H), 7.87 (m, Ar$\underline{H}$, 1H) and 8.67 (d, Ar$\underline{H}$, 1H).

Preparation of Compound 9

A mixture of 539 mg (1.0 mmol) of diiodide 8, 1.2 g (5.5 mmol) of boronic acid 3, 50 mg (0.04 mmol) of tetrakis(triphenylphosphine)palladium, 5 mL of EtOH, 10 mL of 2M aqueous $Na_2CO_3$, and 20 mL of benzene under Ar was refluxed for 8 h, cooled at 25°, and diluted with benzene (100 mL) and 10% NaCl (300 mL).* The organic layer was dried, concentrated to 15 mL, and added to an alumina column (75 g) made up in 1:1 benzene-hexane. Elution of the column with benzene (2 L) gave 528 mg (79%) as a colorless glass. The mass spectrum gave the expected molecular ion at m/e 671. The $^1H$ NMR spectrum (200 MHz, $CDCl_3$) gave absorptions at δ 0.77-1.32 (m, $CH_2C\underline{H}_3$, 18H), 2.34 (s, ArC$\underline{H}_3$, 3H), 2.35 (s, ArC$\underline{H}_3$, 3H), 3.47-3.68 (m, $OC\underline{H}_2CH_3$, 12H), 4.58 (s, ArC$\underline{H}$, 4H), 7.24-7.44 (m, Ar$\underline{H}$, 7H) and 8.27 (m, Ar$\underline{H}$, 2H).
*Modeled after Miyoura, N.; Yanagi, T.; Suzuki, A., *Syn. Comm.* 1981, 11(7), 513-519.

Preparation of Compound 10

To a mixture of 740 mg (1.1 mmol) of 9 in 20 mL of $C_6H_6$ and 20 mL of aqueous 1N NaOH under Ar was added 0.53 g (2.7 mmol) of $Fe(CO)_5$[3]. The mixture was stirred for 8 h at 25° C., 100 mL of $C_6H_6$ was added and the suspension was filtered through Celite. The benzene layer was dried ($Mg_2CO_3$), concentrated to 20 mL, and added to an alumina column (100 g made up in $CH_2Cl_2$). Elution of the column with 9:1 and 4:1 $CH_2Cl_2$—$Et_2O$ mixtures (2 L each) gave 550 mg (78%) of 10 as a light-brown foam. The mass spectrum (70 eV) gave the expected molecular ion at m/e 641. The $^1H$ NMR spectrum (200 MHz, $CDCl_3$) gave absorptions at δ 0.70-1.31 (m, $CH_2C\underline{H}_3$ 18H), 2.32 (s, ArC$\underline{H}_3$, 3H), 2.33 (s, ArC$\underline{H}_3$, 3H), 3.34.-3.71 (m, $OC\underline{H}_2 CH_3$, 12H), 4.59 (s, ArC$\underline{H}_2$, 4H), 6.70-6.80 (m, Ar$\underline{H}$, 2H), and 7.07-7.43 (m, Ar$\underline{H}$, 7H).
[3] Abbayes, H.; Alper, H. *J. Am. Chem. Soc.* 1977 99, 98-101.

Preparation of Compound 11

A mixture of 550 mg (0.86 mmol) of 10, 250 mg (1.14 mmol) of picryl chloride (CTC Organics) and 72 mg (0.86 mmol) of $NaHCO_3$ in 45 mL of $CH_3OH$ under Ar at 25° C. was stirred for 4 h, evaporated at 30° C./20 mm, and the residue was dissolved in $CHCl_3$—$H_2O$ (100 mL of each). The $CHCl_3$ layer was dried, concentrated to 10 mL and added to a silica gel column (75 g) made up in $CH_2Cl_2$. Elution of the column with 500 mL of $CH_2Cl_2$ gave unreacted picryl chloride. Further elution with 19:1 $CH_2Cl_2$—$Et_2O$ (1 l) gave 700 mg (92%) of 11 as an orange foam. The mass spectrum gave the expected molecular ion at m/e 850. The $^1H$ NMR spectrum (200 MHz, $CDCl_3$) gave absorptions at δ 0.76-1.31 (m, $CH_2C\underline{H}_3$, 18H), 2.33 (s, ArC$\underline{H}_3$, 3H), 2.34 (s, ArC$\underline{H}_3$, 3H), 3.51-3.71 (m, $OC\underline{H}_2CH_3$, 12H), 4.58 (s, ArC$\underline{H}_2$, 4H), 7.08-7.38 (m, Ar$\underline{H}$, 9H), 9.06 (s, Ar$\underline{H}$ (picryl), 2H) and 10.32 (s, N$\underline{H}$, 1H).

Preparation of Compound 12

Anhydrous HBr gas was bubbled into a solution of 700 mg (0.82 mmol) of 11 in 250 mL of $CHCl_3$ for 10 min. After stirring an additional 10 min, the solution was poured into 800 mL of $H_2O$ and stirred an additional 30 min. The organic layer was dried, concentrated to 10 mL and flash chromatographed on 60 g of silica gel made up in $CH_2Cl_2$. Elution of the column with $CH_2Cl_2$ gave 720 mg (95%) of 12 as an orange foam. The mass spectrum (70 eV) showed a molecular ion at m/e 920 ($^{79}Br$). The $^1H$ NMR spectrum (200 MHz, $CDCl_3$) gave absorptions at δ 0.77–1.27 (m, $CH_2CH_3$, 12H), 2.33 (s, $ArCH_3$, 6H), 3.48–3.76 (m, $OCH_2CH_3$, 8H), 4.62 (s, $ArCH_2$, 4H), 7.08–7.40 (m, $ArH$, 9H), 9.07 (s, $ArH$ (picryl), 2H) and 10.32 (s, $NH$, 1H).

Preparation of Compound 13

To a refluxing suspension of 1.8 g (37.5 mmol) of NaH (50% mineral oil) in 150 mL of THF under Ar was added a solution of 0.75 g (0.81 mmol) of 12 and 115 mg (0.87 mmol) of cis-2,5-bishydroxymethyl-tetrahydrofuran[3] mm 400 mL of THF over 8 h. The mixture was refluxed an additional 10 h, cooled at 25° C., excess NaH was decomposed with $CH_3OH$, and the solvent was evaporated at 30° C./30 mm. The residue was dissolved in 500 mL portions of $CHCl_3$ and 10% aqueous NaCl. The aqueous layer was acidified to pH 1 with 6N HCl (aqueous) and the organic layer was dried, concentrated to 15 mL and added to a silica gel column (100 g) made up in $CH_2Cl_2$. Elution of the column with $CH_2Cl_2$ (1.5 L) gave 278 mg (37%) of 12. Further elution of the column with 9:1 and 3:1 $CH_2Cl_2$—$(CH_3)_2CO$ mixtures (2 L of each) gave 110 mg (15%) of 13 as an orange-red foam. The mass spectrum (70 eV) gave the expected molecular ion at m/e 892. A FAB mass spectrum (m-nitrobenzyl alcohol dispersion) gave a molecular ion as well as $M+18(M+H_2O)$, $M+23(M+Na)$, and $M+39(M+K)$. The $^1H$ NMR spectrum (200 MHz, $CDCl_3$) gave peaks at δ 0.48–1.13 (m, $CH_2CH_3$, 12H), 1.80–2.33 (m, $ArCH_3$, $CH_2CH_2$, 10H), 3.30–4.82 (m, $OCH_2$, $CH_2CHO$, 18H), 7.03–7.28 (m, ArH, 9H), 9.09 (s, $ArH$ (picryl), 2H) and 10.36 (s, NH, 1H).

[3] Prepared in accordance with Timko, J. M.; Moore, S. S.; Hiberty, P. C.; Cram, D. J. *J. Am. Chem. Soc.* 1977, 99–4207.

10.2. Synthesis of a Second Preferred Chromogenic Hemispherand

An experiment was performed to synthesize another preferred embodiment of compound (I), supra. The chromogenic hemispherand prepared in this experiment is depicted as compound 18 in the reaction pathway in FIG. 2.

Preparation of Compound 14

To a mixture of 1.3 g (2.8 mmol) of 6 and 2.6 (11 mmol) of crude 3 in 25 mL of benzene and 6 mL of ethanol under Ar was added 12 mL of aqueous 2M $Na_2CO_3$. To this vigorously stirred mixture was added 150 mg (0.13 mmol) of tetrakis(triphenylphosphine)palladium (0). After 24 h of reflux, a fresh 50 mg portion of catalyst was added and refluxing was continued for 24 h. The mixture was cooled at 25° C., diluted with benzene (200 mL) and 10% aqueous NaCl (100 mL), the layers were separated, and the organic layer was dried and evaporated. The residue was dissolved in 25 mL of $CH_2Cl_2$ and chromatographed on 200 g of alumina made up in benzene. Elution of the column with ether gave 1.3 g (74%) of 14 as a colorless oil. The mass spectrum (70 eV) showed a molecular ion at m/e 626. The $^1H$ NMR spectrum (200 MHz, $CDCl_3$) showed absorptions at δ 0.76–1.31 (m, $OCH_2CH_3$, 15H), 2.32 (s, $ArCH_3$, 3H), 2.33 (s, $ArH_3$, 3H), 3.43–3.67 (m, $OCH_2$, 10H), 4.59 (s, $ArCH_2$, 4H) and 7.13–7.44 (m, $ArH$, 10H).

Preparation of Compound 15

Anhydrous HBr gas was bubbled into a solution of 340 mg (0.54 mmol) of 14 in 100 mL of $CHCl_3$ for 15 min. After stirring an additional 15 min, the solution was poured into 800 mL of $H_2O$ and stirred an additional 30 min. The organic layer was dried, concentrated to 10 mL and flash chromatographed on 60 g of silica gel made up in $CH_2Cl_2$. Elution of the column with $CH_2Cl_2$ gave 300 mg (83%) of 15 as a colorless foam. The mass spectrum (70 eV) showed a molecular ion at m/e 666 $-Br^{79}$. The $^1H$ NMR spectrum (200 MHz, $CDCl_3$) gave absorptions at δ 0.80 (t, $CH_2CH_3$, 3H), 1.07–1.21 (m, $CH_2CH_3$, 6H), 2.31 (s, $ArCH_3$, 3H), 2.34 (s, $ArCH_3$ 3H), 3.40–3.84 (m, $OCH_2$, 6H), 4.62 (s(b), $ArCH_2$, 4H) and 7.06–7.53 (m, $ArH$, 10H).

Preparation of Compound 16

To a refluxing suspension of 3.0 g (62.5 mmol) of NaH (50% in mineral oil) in 400 mL of THF under Ar was added to a solution of 3.0 g (4.5 mmol) of 15 and 610 mg (4.6 mmol) of cis-2,5-bishydroxymethyltetrahydrofuran in 800 mL of THF over 8 h. The mixture was refluxed for an additional 16 h, cooled to 25° C., excess NaH decomposed with $CH_3OH$, and the solvent was evaporated at 30°/30 mm. The residue was dissolved in 500 mL portions of $CHCl_3$ and 10% NaCl, acidified to pH~3, and the organic layer was separated, dried, concentrated to 15 mL, and added to a silica gel column (150 g) made up in $CH_2Cl_2$. Elution of the column with $CH_2Cl_2$ (1 L) and 19:1 and 9:1 $CH_2$-acetone (2 L of each) gave traces of unidentified material. Further elution of the column with 4:1 and 7:3 $CH_2Cl_2$-acetone mixtures (2 L of each) gave 730 mg (25%) of 16 as a white foam. The mass spectrum (70 eV) gave the expected molecular ion at m/e 638. The $^1H$ NMR spectrum (200 MHz, $CDCl_3$) gave absorptions at δ 0.76 (t, inner $OCH_2CH_3$, 3H), 0.98–1.18 (m, outer $OCH_2CH_3$, 6H), 1.53–2.41 (m, $ArCH_3$, $CH_2CH_2$, 10H), 3.38–4.65 (m, $OCH_2$, $CH_2CHO$, 16H) and 7.03–7.42 (m, $ArH$, 10H).

Preparation of Compound 17

To a solution of 1.5 g (3.4 mmol) of $Tl(NO_3)_3 \cdot 3H_2O$ in 20 mL of $CH_3OH$ was added 470 mg (0.74 mmol) of phenol 16 in 20 mL of $CHCl_3$. After stirring 30 min, the suspension was diluted with 200 mL portions of $CHCl_3$ and 10% aqueous NaCl. The layers were separated and the organic layer was dried, concentrated to 15 mL and chromatographed on 125 g silica gel made up in $CH_2Cl_2$. Elution of the column with $CH_2Cl_2$-acetone mixtures (85:15 and 70:30) gave 369 mg (77%) of quinone 17 as an orange foam. The mass spectrum (70 eV) gave the expected molecular ion at m/e 652. The $^1H$ NMR spectrum (200 MHz, $CDCl_3$) gave absorptions at δ 0.88 (t, $OCH_2CH_3$, 3H), 1.06 (t, $OCH_2CH_3$, 3H), 1.23 (t, $OCH_2CH_3$, 3H), 1.68–2.42 (m, $ArCH_2$, $CH_2CH_2$, 10H), 3.44–4.22 ($OCH_2$, $CH_2CHO$, 12H), 4.62 (m, $ArCH_2$, 4H) and 6.96–7.48 (m, $ArH$, $CHCOCH$, 9H).

Preparation of Compound 18

To a solution of 290 mg (0.44 mmol) of quinone 17 in $CHCl_3$ (1 mL) and EtOH (22 mL) was added 172 mg (0.87 mmol) of 2,4-dinitrophenylhydrazine (as its $H_2SO_4$ salt in 3 mL of EtOH). After stirring 5 min at 25° C., the mixture was heated to 80° C. over 12 min, and then cooled to 25° C. The solution was diluted with 400 mL of $CHCl_3$ and 600 mL of deionized $H_2O$. The organic layer was extracted with 3×500 mL portions of deionized $H_2O$ and evaporated at 30° C. under reduced pressure. The residue was dissolved in 300 mL of benzene and evaporated at 30° C. to remove adventitious $H_2O$. The residue was dried at 25° C. under high vacuum and then purified by gel permeation chromatography. A gel permeation chromatography column, 20 ft×0.375 in outer diameter packed with 200 g of 100 Å styragel (Waters Associates) with $CH_2Cl_2$ as the mobile phase at flow rates of 4 mL/min, was used. A fraction with retention volume of 134 mL was collected and evaporated to give 243 mg (67%) of 18 as a red foam. The $^1$H NMR spectrum (200 MHz, $CDCl_3$ gave absorptions at δ 0.75–1.17 (m, $OCH_2C\underline{H}_3$, 9H), 1.60–2.39 (m, $ArCH_3$, $C\underline{H}_2CH_2$, 10H), 3.44–4.67 (m, $OC\underline{H}_2$, $CH_2C\underline{H}O$, 16H) and 7.15–8.79 (m, $Ar\underline{H}$, 12H).

10.3. A Preferred Aqueous System for Potassium Determination

An experiment was conducted to assess the performance of the present invention in the analysis of potassium ion in an aqueous system, in a presently preferred embodiment.

Accordingly, a reagent solution of the invention was prepared by dissolving 8.9 mg of compound (IV), Section 6.3, in 60 mL diethyleneglycolmonoethyl ether. To this was added 40 mL of 0.1M CHES[1] buffer (pH=8.6) and the mixture thoroughly stirred.

[1] CHES buffer is prepared by dissolving 2.1 g of cyclohexylaminoethane sulfonic acid in 90 mL deionized water, adding sufficient 1M tetramethylammonium hydroxide to bring the pH to 8.6, and adding deionized water to bring the volume to 100 mL A Beckman DU-8 spectrophotometer was used for the analysis of the potassium ion. To perform the assay, 0.99 mL of the above reagent composition was pipetted into an optical cuvette followed by 0.01 mL of the aqueous potassium sample. After thorough mixing, the absorbance of the resulting solution was measured at 450 nm wavelength.

The spectrophotometric data obtained from this procedure is shown in Table 1, wherein the change in light absorbance at 450 nm (Δ A 450 nm) vs the potassium concentration is recorded.

It can be clearly seen that Δ A 450 nm increases in proportion to increase in potassium ion concentration in the assay sample, affording a quantitative determination of the potassium ion in the sample.

TABLE 1

Potassium Response to Compound (IV) in Mixed Solvent System

| | mM,K+ | ΔA450 nm |
|---|---|---|
| 1 | 0.0 | 0.0000 |
| 2 | 2.0 | 0.0264 |
| 3 | 4.0 | 0.0639 |
| 4 | 6.0 | 0.0792 |
| 5 | 8.0 | 0.1117 |
| 6 | 10.0 | 0.1339 |

10.4. A Preferred Liquid/Liquid Partitioning System for Potassium Assay

An experiment was conducted to study the assay of potassium ion in an aqueous test sample by a liquid/liquid partitioning system in which the potassium ion is extracted into an organic solvent that is immiscible with the aqueous phase.

A stock buffer solution was prepared by dissolving 4.2 g CHES (cyclohexylaminoethane sulfonic acid) into 80 ml of deionized water, adjusting the pH to 9.5 with 1M tetramethylammonium hydroxide and bringing the total volume to 100 ml with deionized water in a volumetric flask.

A stock solution of compound (IV) was prepared by dissolving 9 mg of the compound in 100 ml of dichloromethane.

In an assay procedure, 2 ml of the stock buffer solution, 2 ml of the stock solution of compound IV and 1 ml of a standard potassium chloride solution were pipetted into a test tube and thoroughly agitated on a vortex mixer for 1–2 minutes. The test tube was set aside briefly to allow phase separation. The organic methylene chloride phase was transferred to an optical cuvette and the absorbance was measured at 300–700 nm on a Beckman DU-8 spectrophotometer. A control was provided by assaying deionized water as a blank sample. In addition, an aqueous standard sodium chloride sample was also assayed by the above procedure in order to assess the selectivity of compound (IV) for potassium over sodium.

The results of the above experiments are depicted in FIG. 3. As evident there is very little spectral change for the sodium ion sample but a substantial change for the potassium ion sample as compared to the blank control. Thus, the results clearly indicate high selectivity of compound (IV) for potassium over the sodium ion.

In further experiments, a series of aqueous standards of potassium chloride with concentrations ranging between 0 to 10 mM (millimolar) were assayed by the above procedure. For each potassium standard solution the change in absorbance at 440 nm (Δ A 440 nm) against a blank control was measured on a Beckman DU-8 spectrophotometer.

The results are depicted in Table 2 and indicate an increase in Δ A 440 nm with the increasing potassium ion concentration, affording a quantitative determination of potassium ion concentration in a test sample.

TABLE 2

Potassium Response To Compound (IV) In Solvent Extraction

| | mM,K+ | ΔA 440 nm |
|---|---|---|
| 1 | 0.0 | 0.0000 |
| 2 | 2.0 | 0.4235 |
| 3 | 4.0 | 0.5726 |
| 4 | 6.0 | 0.6482 |
| 5 | 8.0 | 0.6797 |
| 6 | 10.0 | 0.7012 |

10.5. A Preferred Test Device

An experiment was performed to prepare a test device of the present invention capable of detecting the presence of potassium, whereby a carrier matrix of high density polyethylene (HDPE) was incorporated with the compound (V) shown below.

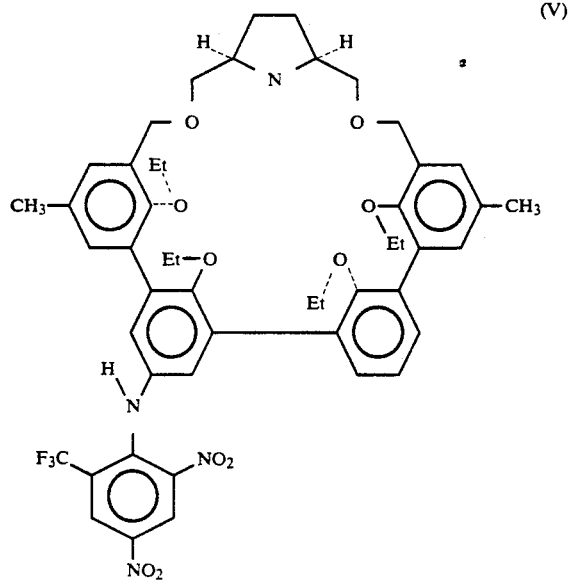

(V)

Porous HDPE disks having a diameter of ½ inch, a thickness of 1/32 inch, and a 35 μm pore size were prepared from sheet material obtained from Porex Technologies, Inc., Fairburn, GA. The disks were then each treated with 30 μl of reagent stock solution. The stock reagent solution comprised a mixture of 1.0 ml cyclohexanone, 0.15 ml tricresyl phosphate, 10 mg cellulose acetate, 15 mg compound (V), 30 mg triethanolamine, 9 mg 2-naphthalene sulfonic acid, and 5 mg Brij-35 (polyethoxylauryl ether).

The treatment comprised depositing on one side of each disk a 30 μl (microliter) aliquot of stock reagent solution, which permeated the entire disk, and allowing the disks to dry at room temperature for five hours with subsequent storage in a dessicator charged with anhydrous calcium sulfate for 2 hours.

The disks were tested by innoculation with 25 μl of analytical specimens. Following 5 minutes incubation with the analytical specimens, the disks were measured for diffuse reflective signal R at 580 nm using an Infra-Alyzer ® (Technicon Instruments Corporation) modified for use in the visible portion of the electromagnetic spectrum.

Reflectance measurements R were transformed into K/S values utilizing the well-known equation of Kubelka and Munk $$K/S = (1-R)^2/2R.$$

K/S values are plotted against potassium concentration in FIG. 4. The dose response curve demonstrates that the test device provides requisite sensitivity for potassium assay in the clinical range of 2–10 mM concentration.

10.6. Use of A Preferred Test Device for Potassium Determination in Serum

An experiment was conducted to compare the test device of the present invention with an art-established procedure for measuring potassium in serum.

A series of random serum samples containing a broad range of potassium concentration was obtained. These were analyzed on an Infra Alyzer ® system as in 10.5, supra, and also by the IL443 ® Flame Photometer (Instrumentation Laboratories, Lexington, MA 02173).

Results

The comparative data is presented in FIG. 5, and shows good correlation between the test device of the present invention and a standard flame photometric method.

What is claimed is:

1. A chromogenic hemispherand having the structure

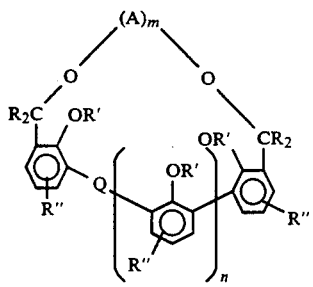

wherein:

R, same or different, is hydrogen, lower alkyl, lower alkylidene, lower alkenyl, allyl or aryl;

R', same or different, is lower alkyl, lower alkylidene, lower alkenyl, allyl or aryl;

R'', same or different, is hydrogen, lower alkyl, lower alkylidene, lower alkenyl, allyl or aryl;

A is an aliphatic ether group or a tetrahydrofuran group;

n is about 0 to 3;

m is 1 to about 3; and

Q is a chromogenic moiety capable of providing a detectable response upon the complexation of said compound with a test cation in a test sample.

2. The chromogenic hemispherand of claim 1 in which the chromogenic moiety Q has the structure

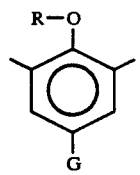

wherein G is 2,4,6-trinitroanilino; 2,6-dinitro-4-trifluoromethylanilino; 2,4-dinitro-6-trifluoromethylanilino; 4-nitroanilino; 4-nitrophenylazo; 4-nitrostyryl; or 4-benzoquinonmonoimino.

3. The chromogenic hemispherand of claim 2 in which the chromogenic moiety Q has the structure

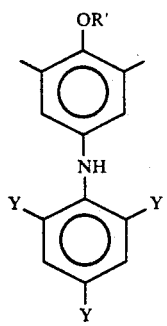

wherein:
Y, same or different, is an electron withdrawing group selected from the group consisting of CN, $NO_2$, $CF_3$, COOR.

4. A composition for detecting the presence of an ion in solution, said composition comprising the compound of one of claims 2, 3, or 1 and a buffer to provide a pH in the range of about 7-11.

5. A method for preparing a chromogenic hemispherand (I) having the structure

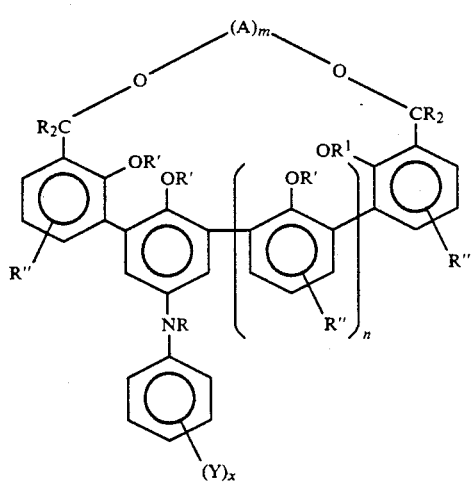
(I)

said method comprising the steps of:
(a) preparing a compound (II) having the structure

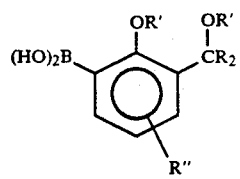
(II)

(b) preparing a compound (III) having the structure

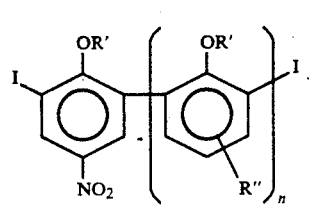
(III)

(c) coupling the compounds (II) and (III) to form a compound (IV) having structure

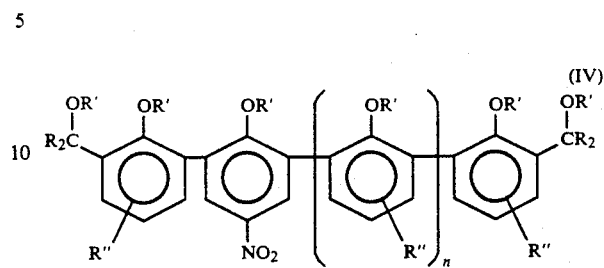
(IV)

(d) subjecting the compound (IV) to reducing conditions to form a compound (V) having the structure

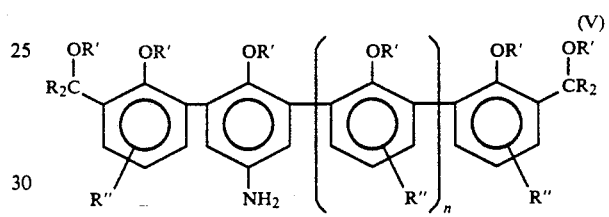
(V)

(e) coupling the compound (V) to a compound having the structure

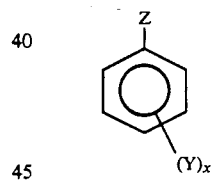

to form a compound (VI) having the structure

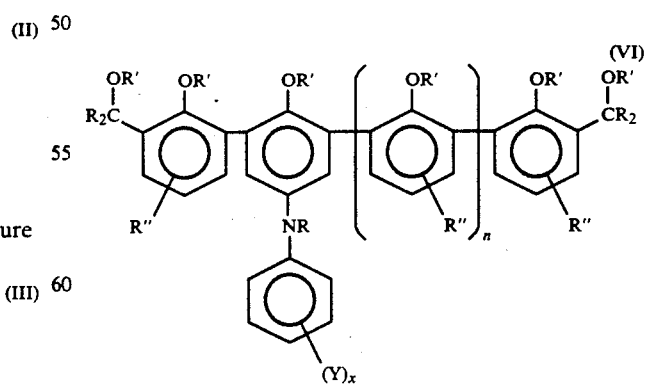
(VI)

(f) halogenating the compound (VI) to form a compound (VII) having the structure

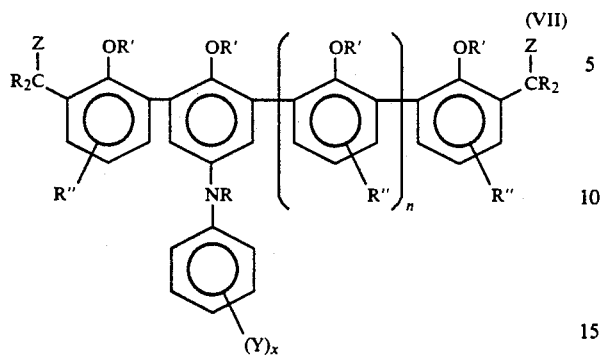

(g) forming the chromogenic hemispherand (I) by coupling the compound (VII) with a diol having the structure

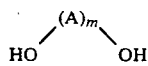

wherein:

R, same or different, is hydrogen, lower alkyl, lower alkylidene, lower alkenyl, allyl or aryl;

R', same or different, is lower alkyl, lower alkylidene, lower alkenyl, allyl or aryl;

R", same or different, is hydrogen, lower alkyl, lower alkylidene, lower alkenyl, allyl or aryl;

Y is an electron withdrawing group;

Z is halogen;

A is an aliphatic ether group or a tetrahydrofuran group m is 1 to about 3;

n is 0 to about 3; and x is 2 to 4

6. The method of claim 5 in which compound (II) is prepared in a synthetic sequence comprising a hydroxyalkylation reaction, an alkylation or arylation reaction, and a lithiation/boronation reaction in accordance with the reaction sequence:

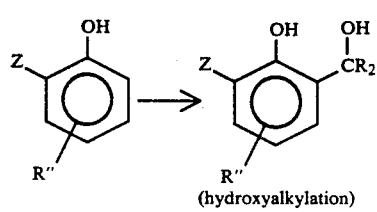

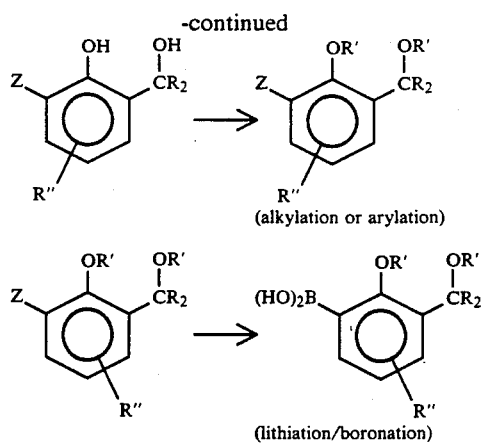

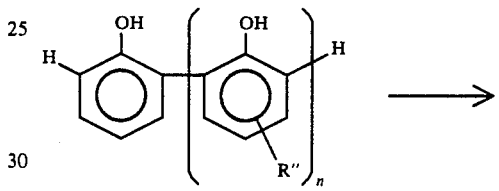

7. The method of claim 5 in which compound (III) is prepared by an alkylation or arylation reaction, and a lithiation/iodination reaction in accordance with the reaction sequence:

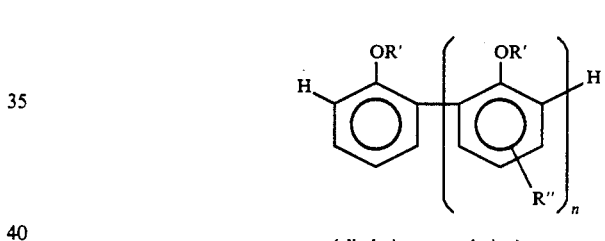

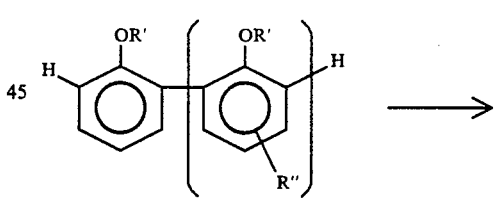

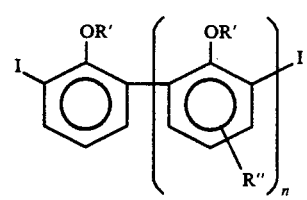

8. The method of claim 5 in which the coupling step is performed by combining the compounds (II) and (III) in the presence of a catalyst, said catalyst comprising tetrekis (triphenylphosphine)palladium thereby forming compound (IV).

9. The method of claim 5 in which the reducing conditions of step (d) comprise iron pentacarbonyl.

* * * * *